(12) United States Patent
Shimazaki

(10) Patent No.: US 6,966,897 B2
(45) Date of Patent: Nov. 22, 2005

(54) COMBINED CONTAINER-SYRINGE AND ASSEMBLY METHOD OF THE SAME

(75) Inventor: Seiji Shimazaki, Takahagi (JP)

(73) Assignee: Arte Corporation, Tokyo (JP)

( * ) Notice: Subject to any disclaimer, the term of this patent is extended or adjusted under 35 U.S.C. 154(b) by 561 days.

(21) Appl. No.: 09/952,298

(22) Filed: Sep. 12, 2001

(65) Prior Publication Data

US 2002/0052577 A1    May 2, 2002

(30) Foreign Application Priority Data

Sep. 22, 2000  (JP) ............................. 2000-289493
Feb. 9, 2001   (JP) ............................. 2001-034684
Apr. 10, 2001  (JP) ............................. 2001-111703

(51) Int. Cl.[7] ............................ A61M 5/32; A61M 5/00
(52) U.S. Cl. ....................... 604/189; 604/192; 604/110
(58) Field of Search ............................ 604/187, 186, 604/164.08, 189–198, 218, 110, 240, 263, 604/199, 206, 208, 211, 97.02, 207, 506

(56) References Cited

U.S. PATENT DOCUMENTS

| 2,569,901 | A |   | 10/1951 | Richard |  |
|---|---|---|---|---|---|
| 4,235,235 | A |   | 11/1980 | Bekkering |  |
| 4,639,250 | A | * | 1/1987 | Rycroft | 604/201 |
| 4,723,938 | A | * | 2/1988 | Goodin et al. | 604/97.02 |
| 4,792,329 | A |   | 12/1988 | Schreuder |  |
| 4,909,788 | A |   | 3/1990 | Egolf |  |
| 5,328,466 | A | * | 7/1994 | Demark | 604/189 |
| 5,423,756 | A | * | 6/1995 | van der Merwe | 604/110 |
| 5,616,134 | A |   | 4/1997 | Firth et al. |  |
| 5,741,236 | A | * | 4/1998 | Kakiuti | 604/192 |

* cited by examiner

Primary Examiner—Nicholas D. Lucchesi
Assistant Examiner—Roz Maiorino
(74) Attorney, Agent, or Firm—Kolisch Hartwell, P.C.

(57) ABSTRACT

The present invention provides a combined container-syringe comprising a syringe body containing a cylindrical-shaped cylinder; a cylindrical tip provided at the anterior end of said cylinder; a finger grip fitted to the posterior end of the cylinder; an injection needle fitted to the cylindrical tip; and a protector covering said injection needle. In addition, the present invention provides a method of assembling a combined container-syringe characterized in comprising an injection needle assembly preparatory process of preparing an injection needle assembly; a detection process of detecting the position of the cutting surface; a mark display process of indicating the detected position of the cutting surface; an aligning process of aligning the positions of the mark and a scale display provided on the exterior portion of the cylinder, on the circumference of the cylinder; and a fitting process of fitting the injection needle assembly to the cylindrical tip.

11 Claims, 13 Drawing Sheets

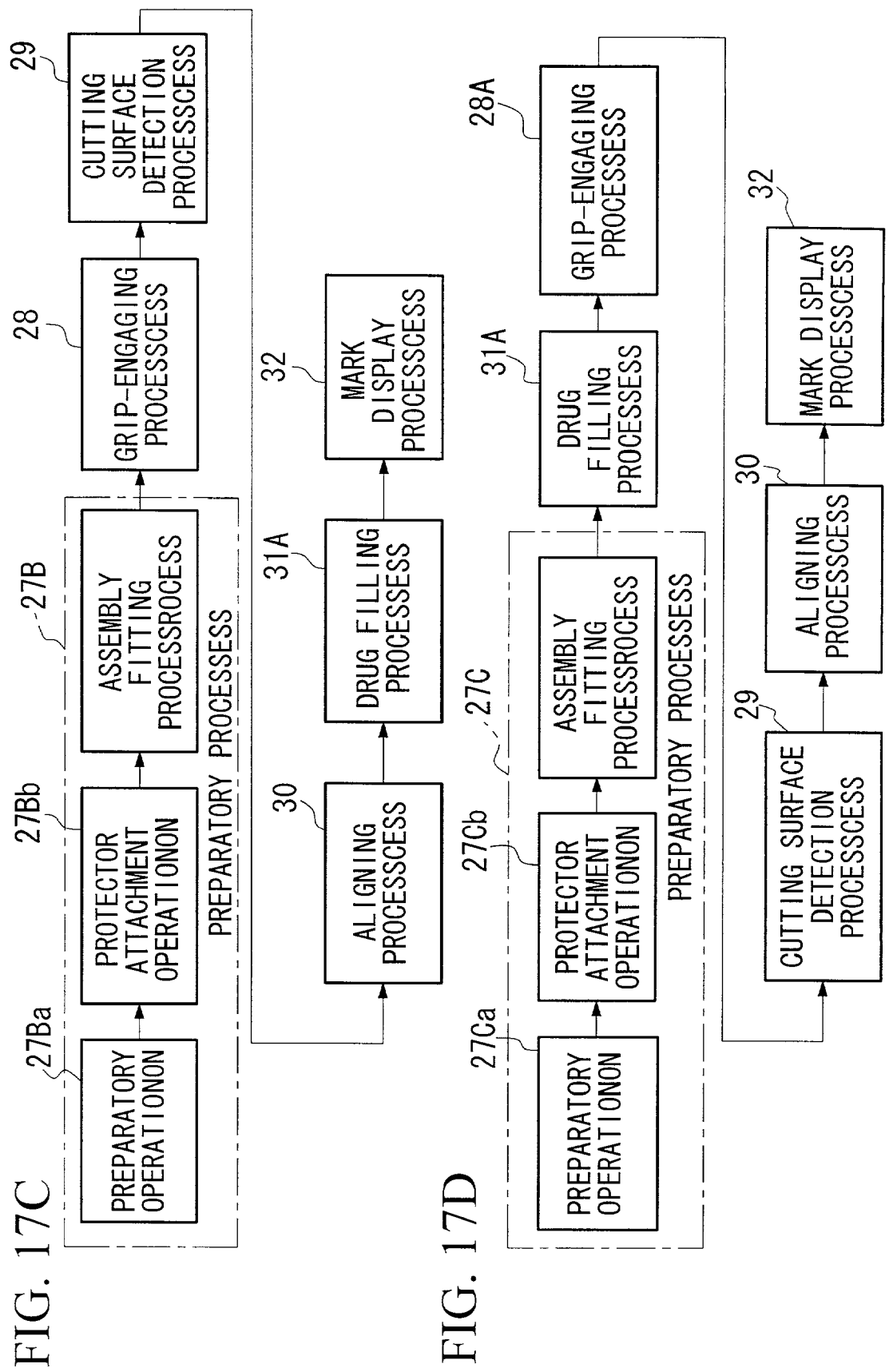

FIG. 20A
FIG. 20B
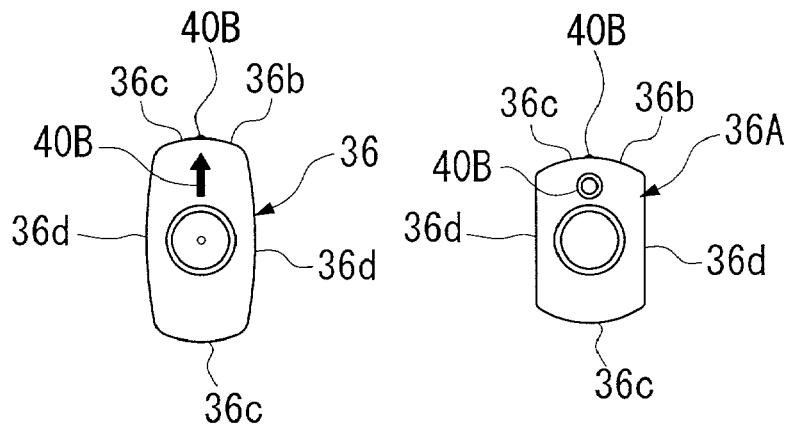
FIG. 21A
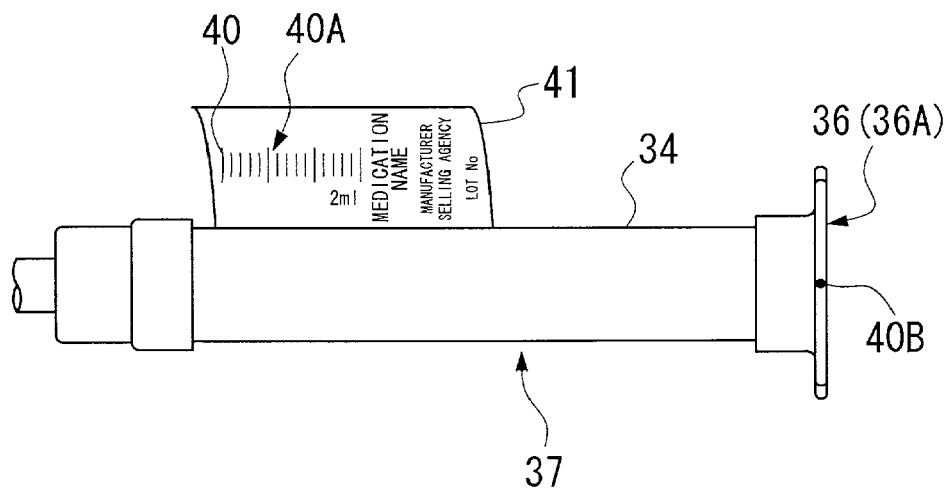
FIG. 21B
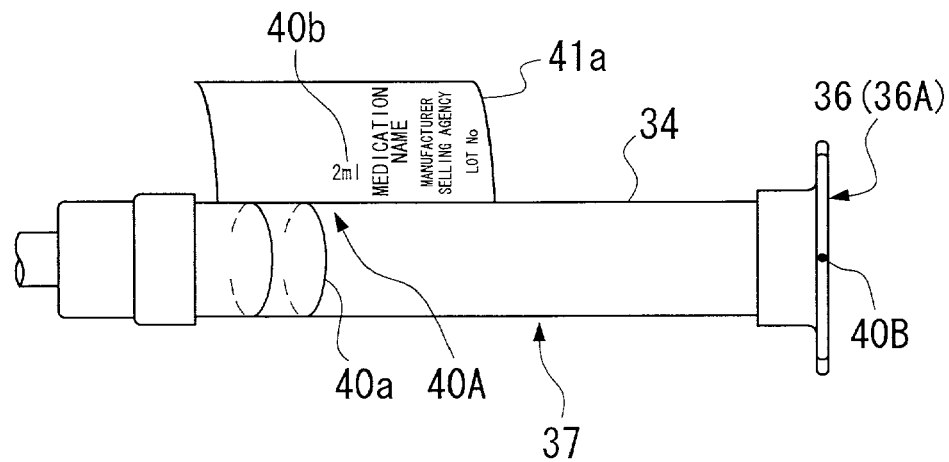

COMBINED CONTAINER-SYRINGE AND ASSEMBLY METHOD OF THE SAME

BACKGROUND OF THE INVENTION

1. Field of the Invention

The present invention relates to a combined container-syringe which can be pre-filled with a drug, stored, and immediately used after removal from the packaging at the time of usage, and an assembly method of the same.

2. Description of Related Art

Combined container-syringes, in which an injection needle is pre-fitted to the tip of a syringe body, can be immediately used upon removal from the packaging material without complicated operations. Recently, these combined container-syringes are enjoying wide use in hospital settings due to their superior convenience and ability to reduce the work of physicians and nurses alike.

However, with regard to the conventional combined container-syringe, the injection needle is randomly assembled with respect to the syringe body, such that, in general, the positions on the circumference of the syringe body of the numbers showing the scale and capacity, characters, medication name, and other important information displayed on the syringe body; cutting surface of the injection needle; and finger rest of the finger grip attached to the posterior end of the syringe body are not aligned with each other. Hence, currently, a method does not exist for assembling a combined container-syringe, in which the positions of the aforementioned display, cutting surface of the injection needle, and finger rest of the finger grip are automatically confirmed and mechanically aligned.

In particular, with regard to conventional combined container-syringes which use the luer lock method (i.e., construction in which the injection needle cannot suddenly come out of the syringe body during injection) employing a screw in the tip of the syringe body, when screwing the injection needle into the tip of the syringe body, the attachment position of the aforementioned is the location at which, depending on the screw, the needle rests after undergoing tightening using a fixed force. This attachment position is not a fixed position wherein the injection needle is compulsively set and fixed into a predetermined positional relationship with respect to the circumference of the syringe body. Consequently, it is not possible to perform minor adjustments to align the positions of the cutting surface of the injection needle, the finger rest of the finger grip, display scale, and the like with each other.

As a result, with respect to these combined container-syringes in which the positions of the cutting surface of the injection needle, the finger rest of the finger grip, display scale, and the like are not in alignment with each other, it is necessary for physicians and nurses to loosen the injection needle attached to the syringe body from the tip of the syringe body, and confirm the orientation of the cutting surface of the injection needle from outside of the protector covering the injection needle. It is then necessary to adjust the cutting surface of the injection needle to the positions of the finger rest of the finger grip, display scale, and the like, and re-fix the injection needle into the tip of the syringe body prior to use. With this action, the convenience and safety of the device are lost, such that improvements thereof are in great demand.

In particular, when the tip of the syringe body uses the aforementioned luer lock method, it is not possible to determine where to orient and fix the position of the cutting surface of the injection needle, which has been assembled with respect to the relationship between the screw position, tapered portion of the tip (luer tip), and thickness of the injection needle at the needle base. Likewise, it is also not possible to freely adjust the position of the cutting surface of the injection needle, such that even when the cutting surface is oriented in a different direction than that of the display scale and the like, or alternatively is not aligned with the position of the finger rest of the finger grip (flange or collar), the injection must be inconveniently administered in the aforementioned state. In addition, there is also the danger that the user will, at times, forget that the tip utilizes a luer lock mechanism, and attempt to forcibly adjust the positions of the cutting surface of the injection needle with the scale of the syringe body, and the like.

At such times, problems exist such as causing damage to the needle base or luer lock tip screw when forcibly rotating the injection needle to adjust the position of the cutting surface of the injection needle with that of the scale of the syringe body, and the like; and loosening of the lock between the injection needle and syringe body during attempts to adjust the cutting surface with the display scale by rotating the injection needle in the direction opposite that of the screw lock, which in turn, results in leakage of the medication from between the aforementioned tip and needle. In this manner, the preparation of an injection becomes extremely complex.

SUMMARY OF THE INVENTION

In consideration of the aforementioned, it is an object of the present invention to provide a method of assembling a combined container-syringe by means of which it is possible to fit an injection needle to a syringe body with the positions of the scale, cutting surface of the injection needle, and finger rest of the finger grip reliably in alignment with each other on the circumference of the syringe body.

In addition, it is an object of the present invention to also provide a combined container-syringe that is extremely convenient, safe, and easily detachable, wherein the positions on the circumference of the syringe body of the scale, cutting surface of the injection needle, and finger rest of the finger grip are in alignment with each other.

In order to solve the above-described problems, the present invention provides a method of assembling a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; said method of assembling said combined container-syringe is characterized in comprising: an injection needle assembly preparatory process of preparing an injection needle assembly comprising said injection needle and said protector; a detection process of detecting the position of the cutting surface on the circumference of said injection needle in said injection needle assembly from the exterior of said protector; a mark display process of marking and displaying a mark on the exterior of said injection needle assembly indicating the detected position of said cutting surface; an aligning process of aligning the position of said mark formed in said mark display process and the position of a scale display provided on the exterior portion of said cylinder on the circumference of said cylinder; and a fitting process of fitting said injection needle assembly to said cylindrical tip.

In addition, the aforementioned assembly method may further comprise, after completing said fitting process, an adjustment process of engaging said finger grip to the posterior end of said cylinder in a manner that allows rotation, and adjusting the position of said finger grip by rotating said finger grip around the axial circumference of said cylinder, such that the position of a finger rest of said finger grip falls into a predetermined position on the circumference of said cylinder with respect to the position of said mark.

Alternatively, the aforementioned assembly method may further comprise, prior to said fitting process, an adjustment process of engaging said finger grip to the posterior end of said cylinder in a manner that allows rotation, and adjusting the position of said finger grip by rotating said finger grip around the axial circumference of said cylinder, such that the position of a finger rest of said finger grip falls into a predetermined position on the circumference of said cylinder with respect to the position of said display scale.

In addition, the aforementioned assembly method may further comprise, prior to said fitting process, a scale display formation process of forming a scale display by means of adhering a label displaying a scale or the like onto the exterior portion of said cylinder.

After performing said adjustment process of engaging and adjusting the position of said finger grip, said scale display formation process may comprise adhering said label to the exterior portion of said cylinder, such that the position of said label falls into a predetermined position on the circumference of said cylinder with respect to the position of said finger rest of said finger grip.

In addition, in said fitting process of fitting said injection needle assembly to said cylindrical tip, a cylindrical tip that is attachable to the anterior end of said cylinder may be fitted to said injection needle assembly, and said injection needle assembly fitted with said cylindrical tip may then be fitted to the anterior end of said cylinder.

In addition, the aforementioned assembly method may further comprise, prior to said fitting process of fitting said injection needle assembly to said cylindrical tip, an attaching process of attaching a cylindrical tip that is attachable to the anterior end of said cylinder to the anterior end of said cylinder.

The aforementioned cylindrical tip that is attachable to the anterior end of said cylinder may comprise a hub luer lock containing a luer locking member with a luer tapered member and a screw member; and said injection needle assembly may be fitted to said cylindrical tip by means of fitting a needle base attached to said injection needle to said luer tapered member and engaging it with said screw member of said luer locking member.

In addition, the present invention also provides a method of assembling a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; said method of assembling said combined container-syringe is characterized in comprising: an injection needle assembly preparatory process of preparing an injection needle assembly comprising said injection needle and said protector; a detection process of detecting the position of the cutting surface on the circumference of said injection needle in said injection needle assembly from the exterior of said protector; a mark display process of marking and displaying a mark on the exterior of said injection needle assembly indicating the detected position of said cutting surface; a fitting process of fitting said injection needle assembly, which has been marked, to said cylindrical tip; and a scale display formation process of forming a scale display by means of adhering a label displaying said scale or the like onto the exterior portion of said cylinder fitted with said injection needle assembly, in a position on the circumference of said cylinder that is aligned with the position of said mark.

After said fitting process of fitting said injection needle assembly to said cylindrical tip, the aforementioned assembly method may also comprise an engaging process of engaging said finger grip to the posterior end of said cylinder in a manner that allows rotation, and adjusting the position of said finger grip by rotating said finger grip around the axial circumference of said cylinder, such that the position of a finger rest of said finger grip falls into a predetermined position on the circumference of said cylinder with respect to the position of said mark.

Alternatively, in said fitting process of fitting said injection needle assembly to said cylindrical tip, said injection needle assembly may be fitted to said cylindrical tip in a manner such that the position of said mark falls into a predetermined position on the circumference of said cylinder with respect the position of a finger rest of said finger grip which has been fitted to said cylinder.

In addition, prior to said fitting process of fitting said injection needle assembly to said cylindrical tip, it is possible to provide an attaching process of attaching a cylindrical tip, that is attachable to the anterior end of said cylinder, to the anterior end of said cylinder.

The aforementioned cylindrical tip that is attachable to the anterior end of said cylinder may comprise a hub luer lock containing a luer locking member with a luer tapered member and screw member; and said injection needle assembly may be fitted to said cylindrical tip by means of fitting said needle base to said luer tapered member and engaging it with said screw member of said luer locking member.

In addition, the present invention provides a method of assembling a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; said method of assembling said combined container-syringe is characterized in comprising: an injection needle assembly preparatory process of preparing an injection needle assembly comprising said injection needle and said protector; a detection process of detecting the position of the cutting surface on the circumference of said injection needle in said injection needle assembly from the exterior of said protector; an aligning process of aligning said injection needle assembly such that the detected position of said cutting surface and the position of a scale display provided on the exterior portion of said cylinder on the circumference of said cylinder are in alignment; and a fitting process of fitting said aligned injection needle assembly to said cylindrical tip.

In addition, the present invention provides a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; wherein, a mark indicating the position of said cutting surface on the circumference of said injection needle is provided on at least one exterior surface among the exteriors of said cylindrical tip, said protector, and said finger grip; and the position of said mark and the position of a scale display, provided on the exterior portion of said cylinder, are in alignment on the circumference of said cylinder.

The aforementioned cylindrical tip may comprise a hub luer lock that is attachable to the anterior end of said cylinder and contains a luer tapered member and a luer locking member equipped with a screw member, such that said injection needle is fitted to said cylindrical tip via a needle base attached to said injection needle by means of fitting said needle base to said luer tapered member and engaging it with said screw member of said luer locking member; and said mark is provided on the exterior surface of said cylindrical tip.

The aforementioned finger grip may be constructed in a manner as to allow rotation around the axial circumference of said cylinder, such that the position on the circumference of said cylinder of a finger rest of said finger grip can be adjusted.

In addition, the present invention provides a method of assembling a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; said method of assembling said combined container-syringe is characterized in comprising: a fitting process of fitting said injection needle to said cylindrical tip; a grip-engaging process of engaging said finger grip to the posterior end of said cylinder; a detection process of detecting the position, on the circumference of said cylinder, of the cutting surface of said injection needle while rotating said cylinder fitted with said injection needle along the axial circumference thereof; and an aligning process of aligning the position of said finger grip with the position of said cutting surface of said injection needle by means of rotating said finger grip, which is fitted to said cylinder, relative to said cylinder.

The aforementioned assembly method may further comprise, after said aligning process, a mark display process of marking and displaying a mark on the exterior of said cylinder indicating the detected position of said cutting surface.

In the aforementioned mark display process, the position of said cutting surface is marked on the exterior of said cylinder by means of adhering a label displaying a scale or the like onto the exterior portion of said cylinder.

In addition, in the aforementioned assembly method it is possible to further provide, between said aligning process and said mark display process, a drug filling process of filling the interior of said cylinder with a drug.

In the aforementioned assembly method, it is possible to further provide, prior to said grip-engaging process, a drug filling process of filling the interior of said cylinder with a drug, and inserting a plunger into said cylinder, wherein, in said grip-engaging process, said finger grip is engaged to said cylinder from a radial direction by means of utilizing an opening provided radially in said finger grip.

In the aforementioned assembly method, it is possible to further provide, prior to said fitting process of fitting said injection needle to said cylindrical tip, an attaching process of attaching a cylindrical tip that is attachable to the anterior end of said cylinder to the anterior end of said cylinder.

The aforementioned cylindrical tip that is attachable to the anterior end of said cylinder comprises an attachment (portion) utilizing a direct attachment system, a luer tip system, or a luer lock system to said injection needle.

In the aforementioned assembly method it is possible to further provide a process of engaging a transparent or semi-transparent protector, for covering said injection needle, to said cylindrical tip after fitting an injection needle to said cylindrical tip.

In addition, the present invention provides a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; wherein, the positions of said cutting surface of said injection needle and said scale display provided on the exterior portion of said cylinder of said syringe body are in alignment with a predetermined position of said finger grip, on the circumference of said cylinder.

The aforementioned finger grip may be constructed in a manner as to allow rotation of the position of a finger rest of said finger grip, on the circumference of said cylinder, around the axial circumference of said cylinder.

In addition, it is also possible to radially provide an opening in said finger grip.

In addition, the present invention provides a method of assembling a combined container-syringe comprising a syringe body containing a cylindrical-shaped cylinder; a cylindrical tip provided at the anterior end of the cylinder; a finger grip engaged to the posterior end of said cylinder; an injection needle fitted to said cylindrical tip; and a protector covering said injection needle; said method of assembling said combined container-syringe is characterized in comprising: a front assembly preparatory process of preparing a front assembly including said cylindrical tip and said injection needle; an assembly fitting process of fitting said front assembly to the anterior end of said cylinder; a detection process of detecting the position, on the circumference of said cylinder, of the cutting surface of said injection needle while rotating said cylinder fitted with said front assembly along the axial circumference thereof; and an aligning process of aligning a predetermined position of said finger grip with the position of said cutting surface of said injection needle by means of rotating said cylinder with respect to said front assembly.

In the aforementioned assembly method, it is possible to further provide, prior to said aligning process, a process of providing a mark on a smooth surface of said finger grip or a finger rest for identifying the position of the cutting surface of said injection needle.

In the aforementioned assembly method, it is possible to further provide, after said aligning process, a mark display process of marking and displaying a mark on the exterior of said cylinder indicating said position of said cutting surface.

In the aforementioned mark display process, it is possible to mark said position of said cutting surface on the exterior of said cylinder by means of adhering a label displaying a scale or the like onto the exterior portion of said cylinder.

The aforementioned cylindrical tip that is attachable to the anterior end of said cylinder may comprise an attachment (portion) which utilizes a direct attachment system, a luer tip system, or a luer lock system to said injection needle.

In the aforementioned assembly method it is possible to further provide a process of engaging a transparent or semi-transparent protector, for covering said injection needle, to said front assembly, such that in said cutting surface detection process, the position of said cutting surface may be detected from the exterior of said protector.

In the aforementioned assembly method it is possible to further provide a steam sterilization process after said aligning process, wherein said cylindrical tip may comprise polypropylene or poly-4-methylpentene.

BRIEF DESCRIPTION OF THE DRAWINGS

FIGS. 17A to 17D are diagrams each showing the assembly process of a method of assembling a combined container-syringe according to the present invention.

FIGS. 20A and 20B are directional views shown by Arrow X in FIGS. 19A and 19B.

FIGS. 21A and 21B are plane views showing structural examples of the scale, etc. of a syringe body.

DESCRIPTION OF THE PREFERRED EMBODIMENTS

In the following, the combined container-syringe according to the present invention will be further described by means of the preferred embodiments with reference to the figures.

Figure 1:
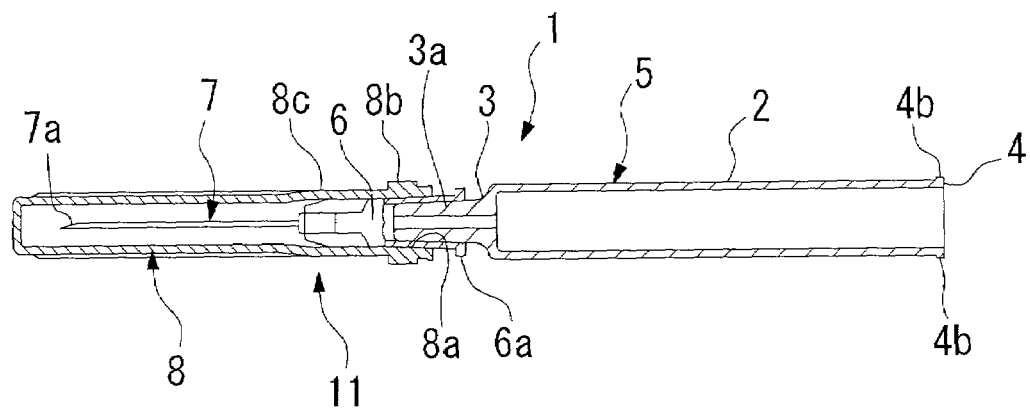
FIG. 1 is a cross-sectional view of a combined container-syringe according to the first embodiment of the present invention.
Figure 2:
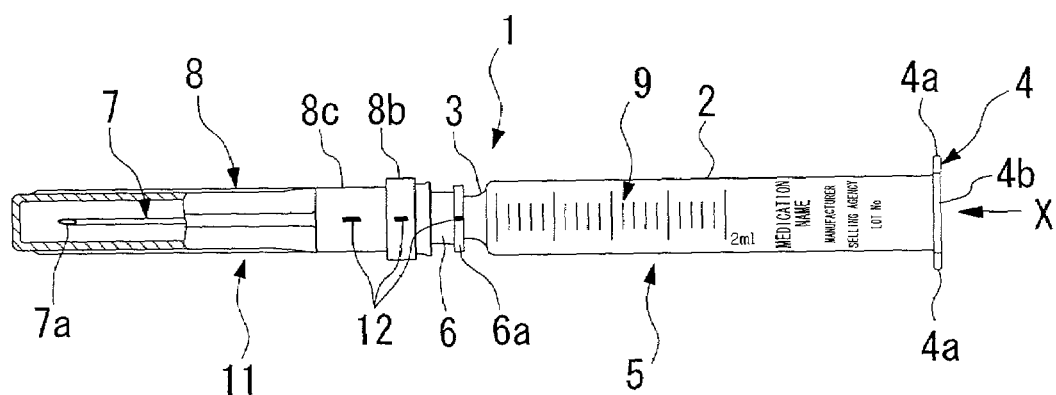
FIG. 2 is a partially cross-sectional view of the combined container-syringe according to the first embodiment of the present invention.
Figure 3:
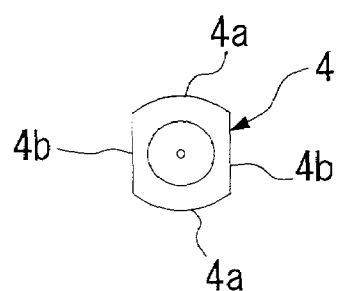
FIG. 3 is a directional view shown by Arrow X in FIG. 2.

FIGS. 1 to 3 show a combined container-syringe 1 according to the first embodiment of the present invention.

This combined container-syringe 1 comprises a syringe body 5 comprising a cylindrical-shaped cylinder 2 with a cylindrical tip 3 provided at the anterior end thereof, and a plunger; a finger grip 4 provided at the posterior end of the aforementioned cylinder 2; an injection needle 7 attached to a needle base (attachment) fitted into the aforementioned cylindrical tip 3; and a protector 8, the opening 8a of which engages to the exterior portion of the needle base 6 of the injection needle, and serves to cover the aforementioned injection needle 7. The aforementioned cylindrical tip 3 of the syringe body 5 and finger grip 4 are formed into a single body with the cylinder 2.

The aforementioned finger grip, as shown in FIG. 3, comprises a pair of finger rests 4a, 4a, and a pair of a smooth surfaces 4b, 4b; the aforementioned smooth surfaces 4b, 4b are each provided at a position that forms a right angle with respect to the position of an aforementioned finger rest 4a, 4a on the circumference of the cylinder 2.

As shown in FIG. 2, a scale display 9 which displays numbers indicating the scale and capacity, characters, medication name, and other vital information, is provided either directly printed or engraved on the exterior surface of the aforementioned cylinder 2. The set position on the circumference of the cylinder 2 of the aforementioned scale display 9 is aligned with the position of either one of the aforementioned smooth surfaces 4b, 4b. In other words, the phase positions of the aforementioned scale display 9 and one of the aforementioned smooth surface 4b are aligned on the circumference of the aforementioned cylinder 2 (i.e., the position of a finger rest 4a of the finger grip 4 is predetermined with respect to the scale display 9 on the circumference of the cylinder 2). Alternatively, it is also possible to align the scale display 9 to the phase position on the circumference of the cylinder 2 of a finger rest 4a of the finger grip 4.

Figure 4A:
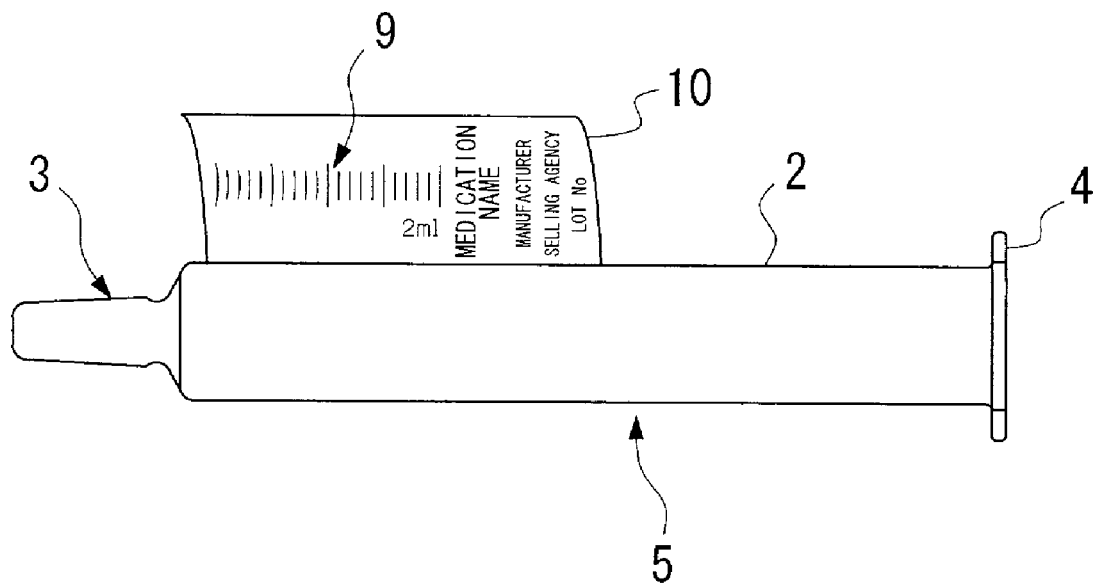
FIGS. 4A and 4B are plane views showing structural examples of the scale, etc. of cylinders.
Figure 4B:
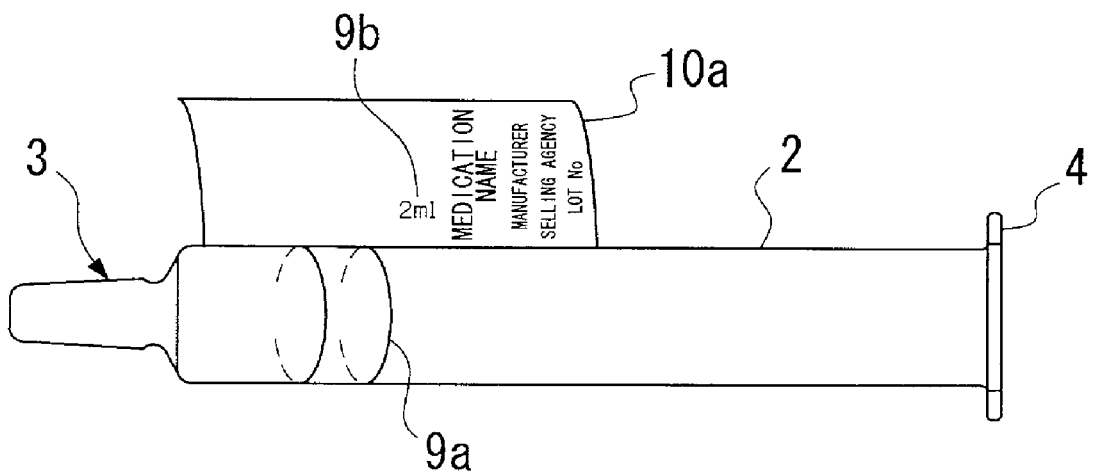

In addition, the aforementioned scale display 9 may alternatively be provided by means of adhering a label 10, onto which the aforementioned scale display 9 has been printed, onto the exterior of the aforementioned cylinder 2, as shown in FIG. 4A. In addition, it is also possible to align part of a scale display 9a with a smooth surface 4b of the finger grip 4, and pre-provide this aligned scale display part 9a on the exterior of the aforementioned cylinder 2, as shown in FIG. 4B. Furthermore, the remaining part of the scale display 9b may be printed onto a label 10 comprising a transparent sheet, and adhered to the exterior surface of the aforementioned cylinder 2 in a manner such that the aforementioned scale display part 9a is visible.

An injection needle assembly 11 comprises the aforementioned injection needle 7, needle base 6 attached to the aforementioned injection needle 7, and protector 8, which is fitted to the aforementioned cylinder 2 via the aforementioned needle base 6. As shown in FIG. 2, in this injection needle assembly 11, the position of the cutting surface 7a of the injection needle tip 7 on the circumference thereof (cutting surface position) is in alignment with at least one exterior surface among the exterior surface of a flange 8b, provided on the opening 8a side of the aforementioned protector 8, the exterior surface of a trunk 8c, and an exterior surface 6a provided on the tip of the aforementioned needle base 6. A mark 12 displaying this above-described position may be printed, engraved, or the like on any of the aforementioned surfaces.

According to the aforementioned combined container-syringe 1, a mark 12 indicating the position of the cutting surface 7a of the injection needle 7 tip on the circumference of the injection needle 7 is provided on the exterior portion of the injection needle assembly 11 comprising a protector 8 which is attached to an injection needle 7 fitted with a needle base 6. As a result, at the time of mechanically fitting the aforementioned injection needle assembly 11 to the aforementioned cylinder 2, it is possible to correctly align the position of the cutting surface 7a of the aforementioned injection needle 7 with the position of the scale display 9, on the circumference of the cylinder 2. In addition, when using this combined container-syringe 1, if by chance the positions of the scale display 9 of the cylinder 2 and mark 12 of the aforementioned injection needle assembly 11, on the circumference of the cylinder 2, are incorrectly aligned, it is possible for the user to easily detect this error, and correctly align the position of the mark 12 to that of the scale display 9.

Consequently, use of an unsafe combined container-syringe 1 comprising an incorrect positional relationship between the finger rest 4a of the finger grip 4 of the cylinder 2 and the cutting surface 7a of the injection needle 7 can be reliably avoided.

Figure 5:
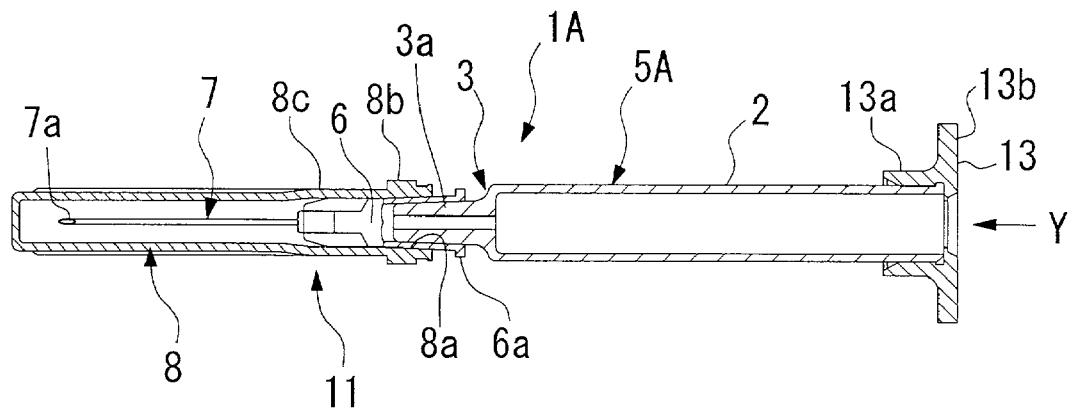
FIG. 5 is a cross-sectional view of a combined container-syringe according to the second embodiment of the present invention.

In the following, a combined container-syringe 1A according to the second embodiment of the present invention will be described with reference to FIG. 5.

This combined container-syringe 1A differs from the aforementioned combined container-syringe 1 in that instead of having the finger grip 4 integrated into a single body with the cylinder 2 as in the combined container-syringe 1 of the aforementioned embodiment, the finger grip 13 is engaged to the cylinder 2 as a separate body, and is engaged in a manner allowing rotation around the axial circumference of the aforementioned cylinder 2. The remaining structures of this combined container-syringe 1A are identical to those of the aforementioned combined container-syringe 1. With regard to the structural components of the aforementioned combined container-syringe 1A, the components that are identical those of the aforementioned combined container-syringe 1 are denoted using the same numeral, and their explanations are omitted.

Figure 6:
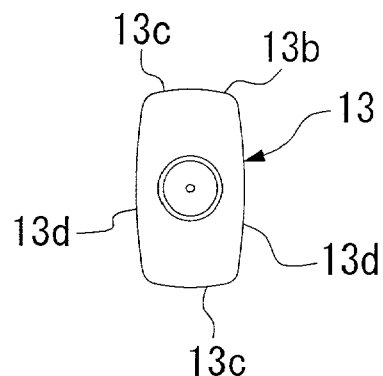
FIG. 6 is a directional view shown by Arrow Y in FIG. 5.
Figure 7:
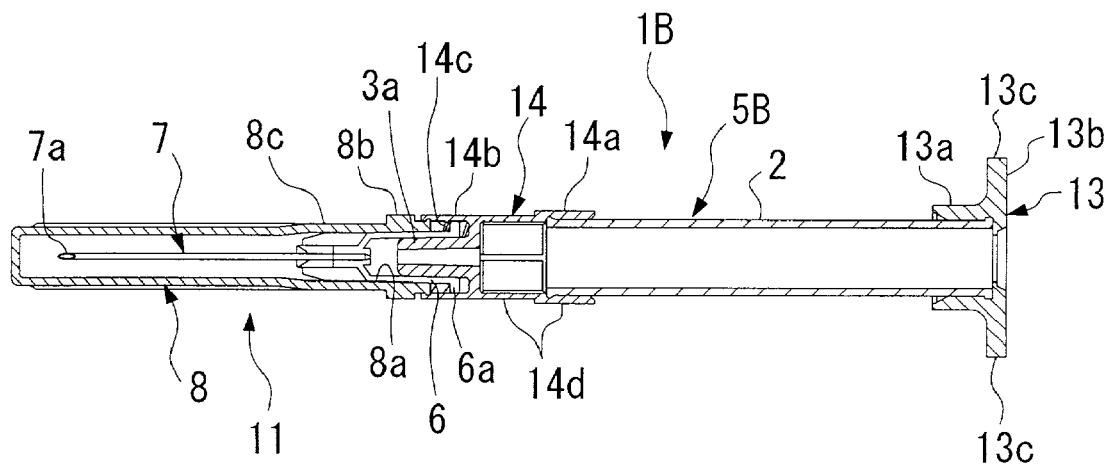
FIG. 7 is a cross-sectional view of a combined container-syringe according to the third embodiment of the present invention.

The aforementioned finger grip 13 comprises a cylindrical member 13a which at its posterior end is integrated into a single body with a roughly rectangular-shaped flange 13b, as shown in FIG. 7. This cylindrical member 13a is engaged to the posterior end of a cylinder 2 in a manner allowing rotation thereof. As shown in FIG. 6, the engagement position of the finger grip 13 on the circumference of the cylinder 2 is set to an angled position where one smooth surface 13d, 13d lying at right angles to the pair of finger rests 13c, 13c of the flange 13b is aligned with a mark 12 and/or scale display 9 of the cylinder 2 (i.e., each of the finger rest 13c is moved into a predetermined position with respect to the scale display 9).

Furthermore, the center portion of the flange 13b is formed slightly smaller than the inner diameter of the aforementioned cylinder 2.

The combined container-syringe 1A according to the present embodiment achieves the same effects and results as the combined container-syringe 1 of the first embodiment.

In the following, a combined container-syringe 1B according to the third embodiment of the present invention will be described with reference to FIG. 7.

This combined container-syringe 1B differs from the aforementioned combined container-syringe 1 in that instead of integrating the aforementioned cylindrical tip 3 into a single body with the cylinder 2 as in the combined container-syringe 1A of the aforementioned second embodiment, a hub luer lock 14 is fitted, as a cylindrical tip, in an attachable manner to the anterior end of the cylinder 2. The aforementioned injection needle assembly 11 is thus fitted to the front end of this hub luer lock 14. The remaining structures of this combined container-syringe 1B are identical to those of the aforementioned combined container-syringe 1A. With regard to the structural components of this combined container-syringe 1B, the components that are identical those of the aforementioned combined container-syringe 1A are denoted using the same numeral, and their explanations are omitted.

This hub luer lock 14 comprises a luer tapered member 3a, having the same shape as the luer tapered member 3a of the aforementioned cylindrical tip 3, which is provided at the front end of a cylindrical engaging member 14a for engaging the anterior end of the cylinder 2, and aligned with the center axis thereof. This hub luer lock 14 also comprises a luer lock 14b provided around the exterior of the luer tapered member 3a with a space thereinbetween. The needle base 6 of the injection needle 7 fits over this luer tapered member 3a, and the external protrusion on the exterior surface 6a of the needle base 6 engages a screw member 14c provided on the inner aspect of the aforementioned luer lock 14b.

According to the present embodiment, other than the protector 8, the aforementioned mark 12 may be provided on the exterior surface of the hub luer lock 14, instead of on the exterior surface 6a of the needle base 6.

According to the aforementioned combined container-syringe 1B, the external protrusion on the exterior surface of the needle base 6 engages the screw member 14c on the inner aspect of the aforementioned luer lock 14b. Therefore, the injection needle 7 can be reliably attached to the cylinder 2, without loosening of the needle base and careless detachment of the injection needle from the cylinder 2 during use.

According to the present embodiment, it is possible to provide the combined container-syringe 1B, wherein, in the same manner as in combined container-syringes 1 and 1A, the positions, on the circumference of the cylinder 2, of the cutting surface 7a of the injection needle 7 and scale display 9 can be correctly aligned.

Figure 8:
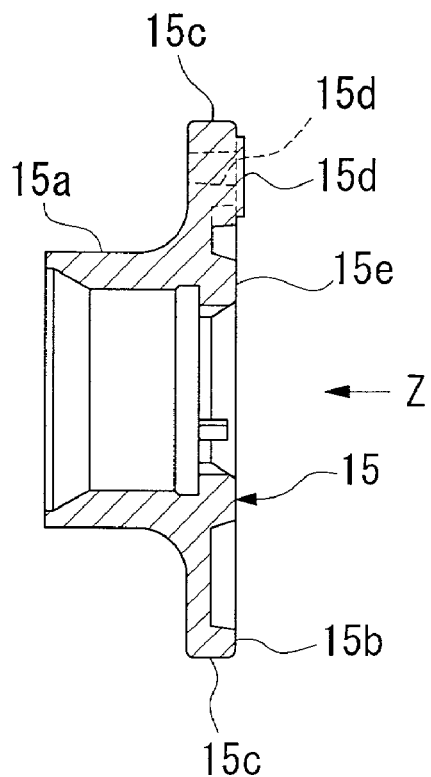
FIG. 8 is a cross-sectional view of another example of a finger grip.
Figure 9A:
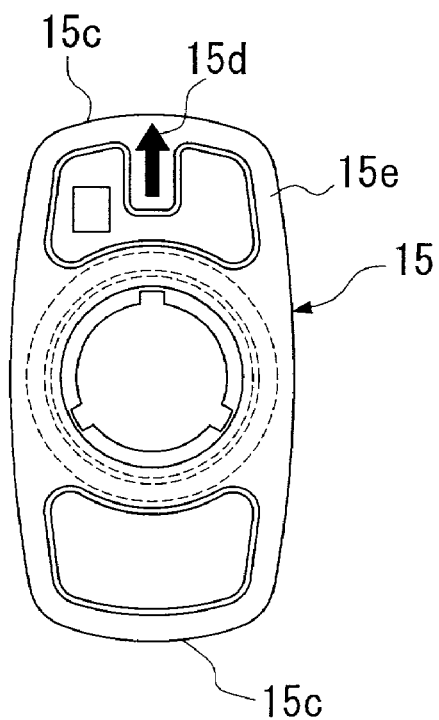
FIGS. 9A and 9B are two examples of directional views of the finger grip shown by Arrow Z in FIG. 8.
Figure 9B:
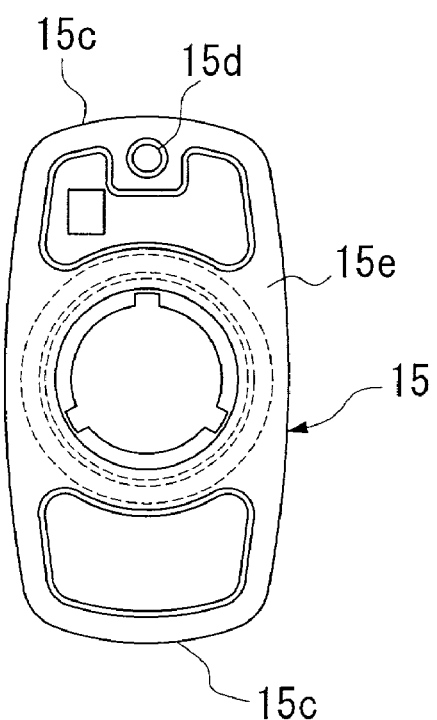

Furthermore, the position of one of the finger rests 15c, 15c of the flange 15b shown in FIGS. 8, 9A and 9B, which is integrated into a single body with the cylindrical portion 15a of the finger grip 15, can be aligned with the position of the mark 12 on the injection needle assembly 11; and a mark 15d indicating the position of the cutting surface 7a of the injection needle 7 can be attached to the back surface of the finger grip 15.

The aforementioned mark 15d, as shown by the solid line in FIG. 8 and FIG. 9A, may be formed as a convex arrow on the exterior, central portion of a finger rest 15c. In addition, as shown by the dashed line in FIG. 8 and FIG. 9B, the mark 15d may also be provided as a circular aperture at the same position. The contour of this mark 15d is not limited to the aforementioned and may comprise a quadrangle or other shape without being particularly limited to an aperture or concave/convex structure. It is also possible to paint the aforementioned mark 15d as well.

In this case, the position of the cutting surface 7a of the injection needle 7 can be easily determined by physicians and nurses from this mark 15d, which is provided on a finger rest 15c of the finger grip 15.

In the following, an assembly method of each of the above combined container-syringes 1, 1A, 1B comprising the aforementioned components will be explained.

In the method of assembling a combined container-syringe 1 according to the first embodiment, an injection needle assembly is first prepared by means of engaging the opening 8a of the protector 8 to the needle base 6 attached to the injection needle 7 and fitting the protector 8 over the exterior of the needle base 6 (preparatory process). Subsequently, the position of the cutting surface 7a (cutting surface position) on the circumference of the injection needle 7 within the aforementioned protector 8 is detected from outside of the protector 8 by means of a detector utilizing an X-ray camera, CCD camera, laser beam or the like. A mark 12 indicating the position of the cutting surface is then either printed or engraved, and displayed (mark display process) on the exterior of the injection needle assembly 11 (e.g., exterior surface 6a of the injection needle 7, exterior surface of the flange 8b, or trunk 8c of the protector 8) by means of an appropriate display unit such as a laser marker or the like.

Subsequently, by means of an appropriate assembly apparatus, the aforementioned injection needle assembly 11 and cylinder 2 are positioned along the same axis with the needle base 6 and cylindrical tip 3 facing each other. The injection needle assembly 11 is then aligned to the cylinder 2 by means of aligning the position of mark 12 displayed on the aforementioned injection needle assembly 11, with the position of the scale display 9 (smooth surface 4b of the finger grip 4) displaying a pre-fixed display on the exterior of the cylinder 2, on the circumference of the cylinder 2, as shown in FIG. 2. Thereafter, the cylindrical tip 3 is inserted into and engaged to the needle base 6 by moving the injection needle 7 and cylinder 2 into proximity with each other (fitting process).

The alignment of the positions of the aforementioned scale display 9 and mark 12, on the circumference of the cylinder 2 is performed, for example, by means of opposing a pair of detectors, formed from the same device as the aforementioned detector, to the aforementioned scale display 9 and mark 12, and attaching them to the aforementioned assembly apparatus such that they form the same angled position on the circumference thereof; monitoring for both the aforementioned scale display 9 and mark 12 while rotating the injection needle assembly 11 and cylinder 2 separately around the axis of the cylinder 2 at a low speed using a rotary unit; and halting the rotation of the injection needle assembly 11 and cylinder 2 when the aforementioned scale display 9 and mark 12 are respectively detected.

In this manner, it is possible to assemble a combined container-syringe 1 in which the positions of the three critical components, the cutting surface 7a of the injection needle 7, the scale display 9 of the cylinder 2, and the smooth surface 4b of the finger grip 4 (with respect to the circumference of the cylinder 2, its position is at a right angle with the finger rest 4a, and pre-aligned with the position of the scale display 9) are aligned in a single direction.

As shown in FIG. 4A, when providing the scale display 9 on the exterior portion of the cylinder 2 by means of adhering a label 10 displaying said scale or the like onto the cylinder 2, the injection needle assembly 11 is fitted to the cylindrical tip 3 with the position of the mark 12 displayed on the injection needle assembly 11 in alignment with the position of the smooth surface 4a of the finger grip 4, on the circumference thereof. Subsequently, using an appropriate label adhering device, the label 10 displaying said scale or the like is adhered onto the exterior portion of the cylinder 2 in a manner such that it is aligned with the mark 12, provided by the aforementioned mark display process, on the circumference of the cylinder 2 (label adhering process).

Alternatively, it is possible to adhere the label 10 displaying said scale or the like onto the exterior portion of the cylinder 2 with the position of the smooth surface 4a of the finger grip 4 aligned thereto (label adhering process), and then fit the injection needle assembly 11 to the aforementioned cylinder 2.

The label adhering process may be selectively performed either before or after the fitting process depending on the circumstances of the assembly method of the combined container-syringe.

Furthermore, it is also possible to align part of the scale display 9a shown in FIG. 4B with the smooth surface 4b of the finger grip 4, and pre-provide this aligned scale display part 9a in a fixed manner on the exterior of the aforementioned cylinder 2. The label 10 displaying the remaining part of the scale display 9b may then be aligned with the aforementioned scale display portion 9a and adhered to the cylinder 2. If the aforementioned label 10 is to be adhered to the cylinder 2 before assembling the combined container-syringe 1, then the assembly of the combined container-syringe 1 may be conducted in the same manner as that shown in FIG. 2, in which a pre-fixed display is provided on the cylinder 2. If the aforementioned label 10 is to be adhered to the cylinder 2 during the assembly of the combined container-syringe 1, then the assembly of the combined container-syringe 1 may be conducted in the same manner as shown in FIG. 4A.

According to the assembly method of the aforementioned combined container-syringe 1, the mark 12 indicating the position of the cutting surface 7a of the injection needle is pre-marked on the exterior of the injection needle assembly, and thus it is possible to assemble the combined container-syringe 1 in which the positions of the cutting surface 7a of the injection needle 7 and the scale display 9 are correctly aligned by means of aligning the position of the scale display 9 to the position of the aforementioned mark 12, on the circumference of the cylinder 2, and fitting the aforementioned injection needle assembly 11 to the cylindrical tip 3. In the same manner, it is possible to provide the combined container-syringe 1 wherein the positions of the three critical components, the cutting surface 7a of the injection needle 7, the scale display 9, and the smooth surface 4b of the finger grip 4 are aligned in a single direction, such that it is not necessary for the physicians and nurses to re-adjust the position of the injection needle 7.

The assembly method of assembling a combined container-syringe 1A according to the second embodiment is similar to the assembly method of the combined container-syringe 1 according to the first embodiment, such that after conducting the preparatory process, mark display process, and fitting process, the finger grip 13 is engaged to the cylinder 2 by means of aligning the position of the smooth surface 13d of the finger grip 13, on the circumference of the cylinder 2, with the position of either the mark 12 of the aforementioned injection needle assembly 11 or the scale display 9 (i.e., such that the finger rest 13c of the finger grip 13 falls into a predetermined position with respect to either the mark 12 or the scale display 9) (see FIG. 2). Alternatively, after engaging the finger grip 13 to the cylinder 2, it is possible to adjust and align the position of the smooth surface 13d of the finger grip 13, on the circumference of the cylinder 2, by means of rotating the finger rest 13c (grip-engaging process).

The aforementioned grip-engaging process and fitting process may be performed sequentially in the above-described manner, or alternatively their sequence may be reversed. In this case, the position of the smooth surface 13d is adjusted on the circumference of the finger grip 13 by means of aligning the smooth surface 13d with the scale display 9.

In the present embodiment, in the case of performing the assembly process by means of adhering the label 10 displaying a scale or the like to the cylinder 2 without pre-displaying said scale on the exterior of the cylinder 2, as shown in FIG. 4A, the injection needle assembly 11 is optionally fitted to the cylinder 2 which does not display a scale or the like (fitting process), and the label 10 is aligned with the position of the mark 12 on the injection needle assembly 11, and adhered to the cylinder 2 (label adhering process). Subsequently, the position of the smooth surface 13d of the finger grip 13 is aligned with the aforementioned mark 12 (scale display portion of label 10), after which the finger grip 13 is engaged to the cylinder 2 (grip-engaging process).

In this case, the above-described fitting process, label adhering process, and grip-engaging process are not limited to the aforementioned, and it is possible to change the sequence of these processes depending on the circumstances surrounding each process, as long as the positions of the aforementioned mark 12, scale display 9, and smooth surface 13d of the finger grip 13 end up in alignment on the circumference of the cylinder 2.

In addition, when the label 10a displaying the remaining part of the scale display 9b shown in FIG. 4B, is adhered to the cylinder displaying a pre-fixed part of the scale display 9a, the injection needle assembly 11 with the mark 12 attached thereon is fitted to the cylinder 2 of a syringe body 5A, and the finger grip 13 is engaged to the cylinder 2, in a manner such that the position of the smooth surface 13d is aligned with the position of the aforementioned mark 12. Subsequently, the aforementioned label 10a is aligned with the position of the aforementioned mark 12 and adhered to the cylinder 2. As a result, it is possible to align the positions of all three components, the aforementioned mark 12, scale display part 9b, and the smooth surface 13d of the finger grip 13.

Furthermore, the scale display part 9a that is fixed and pre-displayed on the cylinder 2 may be positioned without regard to the aforementioned mark 12 (cutting surface 7a); the scale display part 9b, the position of which is critically important, is printed onto the label 10a beforehand, and this label 10a is then aligned with the aforementioned mark 12 and adhered to the cylinder 2 of the syringe body 5A. Consequently, the position of the fixed and pre-displayed scale display part 9a may be unrestricted on the circumference of the cylinder 2.

According to the assembly method of assembling the combined container-syringe 1A of the present embodiment, in addition to achieving the same effects and results as the assembly method of the combined container-syringe 1 of the previous embodiment, due to the fitting of the finger grip 13 in a manner allowing rotation such that the position of the finger rest 13c, on the circumference of the cylinder 2, can be adjusted, it is also possible to appropriately select and perform the process of engaging the finger grip 13 to the cylinder 2 based on the circumstances surrounding the assembly process of this combined container-syringe 1A.

In addition, according to the assembly method of assembling the combined container-syringe 1B of the third embodiment, the hub luer lock 14 serving as an attachable cylindrical tip is attached to the injection needle assembly 11. In the fitting process, the hub luer lock 14 attached with the injection needle assembly 11 is fitted to the anterior end of the cylinder 2. Alternatively, in the fitting process, the hub luer lock 14 that is an attachable cylindrical tip may be attached to the anterior end of the cylinder 2, and the injection needle assembly 11 may then be attached to this hub luer lock 14.

According to the assembly method of assembling the combined container-syringe 1B of the present embodiment, in addition to achieving the same effects and results as the assembly methods for the combined container-syringes 1 and 1A of the previous embodiments, since the aforementioned cylindrical tip is attachable to the aforementioned cylinder 2 like the hub luer lock 14, it is possible to prepare the injection needle assembly 11 of which the injection needle 7 is attached to the cylindrical tip that is detached from the cylinder 2. This injection needle assembly 11 attached with the cylindrical tip can be then reliably fitted to the cylinder 2 by means of aligning the position of the cutting surface 7a of the injection needle 7, on the circumference cylinder 2, with the scale display 9 and/or finger grip 13.

Furthermore, in the assembly methods for the combined container-syringes 1, 1A and 1B of the previous embodiments, the assembly of the combined container-syringe is performed such that the positions of the aforementioned mark 12, scale display 9, smooth surface 4b, 13d of the finger grip, or mark 15d (hereinafter, at least one of these components is referred to as "exterior display member") are in alignment. However, as described in the following, it is also possible to assemble a combined container-syringe without incorporating a mark display process.

For example, a first detector for detecting the cutting surface 7a of the injection needle 7 (cutting surface detector), and a second detector for detecting the exterior display member, such as the scale display 9, the smooth surface 4b, 13d of the finger grip 4, 13, 15, the mark 15d of the finger rest 15c or the like, are placed at positions having identical angles on the circumference of the cylinder 2 with respect to the aforementioned cutting surface 7a and the exterior display member. While monitoring for the cutting surface 7a and the exterior display member using the aforementioned first and second detectors, the injection needle assembly 11 and the cylinder 2 are then rotated by means of a rotary mechanism. The rotation of the injection needle assembly 11 and the cylinder 2 is stopped at the time when the cutting surface 7a and the exterior display member are respectively detected (aligning process). In this manner, it is possible to directly align the positions of the cutting surface 7a and the exterior display member on the circumference of the cylinder 2. Subsequently, by means of a moving device, the injection needle assembly 11 and the cylinder 2 are brought into close proximity with each other, and the injection needle assembly 11 is fitted to cylindrical tip 3 (fitting process).

Furthermore, the aforementioned first and second detectors comprise the same construction as the detector used in the assembly of the combined container-syringe 1 according to the first embodiment.

Even in the present embodiment in which the mark display process is omitted, it is possible to assemble the combined container-syringe by appropriately selecting the sequence of the label adhering process, grip-engaging process, and fitting process of example, in the aforementioned aligning process, when the finger grip 15 onto which the mark 15*d* is attached beforehand to the finger rest 15*c*, it is possible to perform the fitting process by directly aligning the positions of the aforementioned mark 15*d* and the cutting surface 7*a*, and then aligning the label 10 to the position of the aforementioned mark 15*d* and adhering the label to the cylinder 2. In addition, in the case when part of the scale display 9 is fixed and displayed on the cylinder 2, after the fitting process, the aforementioned mark 15*d* and the cutting surface 7*a* are directly aligned in the aligning process. Thereafter, the finger grip 15 may be fitted to the cylinder 2 by means of aligning the aforementioned mark 15*d* with the position of the scale display 9.

According to this assembly method of assembling a combined container-syringe, it is possible to assemble the combined container-syringe by means of detecting the position of the cutting surface 7*a* of the injection needle 7, and directly aligning this position with the position of the exterior display member (i.e., the scale display 9, the smooth surface 13*d* of the finger grip 13, or the mark 15*d*), on the circumference of the cylinder 2. As a result, it is not necessary to include a mark display process, which in turn simplifies the assembly process. It is thus possible to provide an efficient assembly operation for assembling the combined container-syringe.

Figure 10:
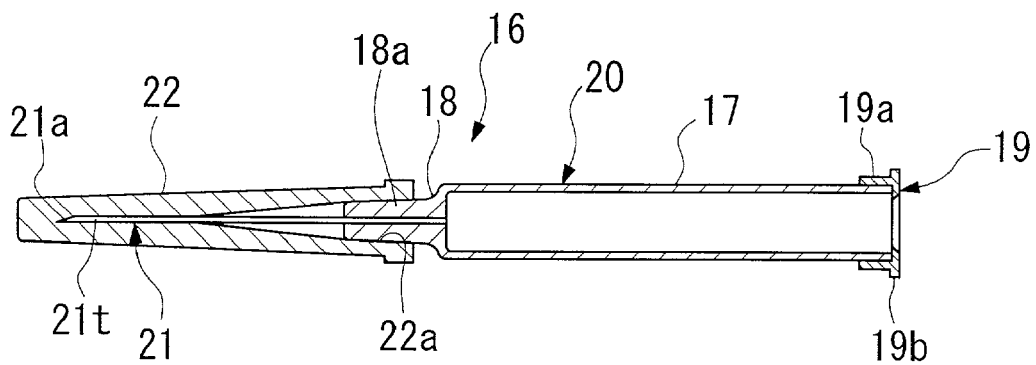
FIG. 10 is a cross-sectional view of a combined container-syringe according to the fourth embodiment of the present invention.
Figure 11:
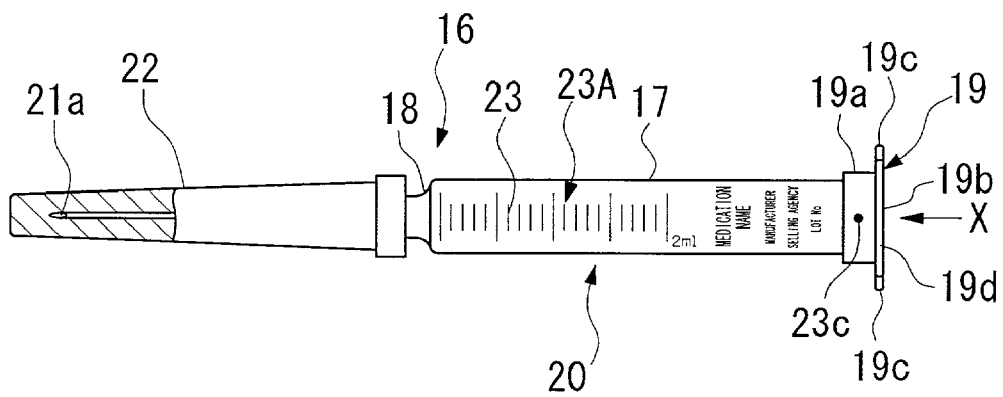
FIG. 11 is a plane view of the combined container-syringe according to the fourth embodiment of the present invention.

FIGS. 10 to 11 show a combined container-syringe 16 utilizing a needle-tube attachment system according to a fourth embodiment of the present invention.

This combined container-syringe comprises a syringe body 20 containing a cylindrical-shaped cylinder 17 integrated into a single body with a cylindrical tip 18 provided at the anterior end thereof and a plunger; a finger grip 19 provided at the posterior end of said cylinder 17; an injection needle 21 attached to the aforementioned cylindrical tip 18 by directly attaching the base end of a needle-tube to said cylindrical tip; and a protector 22, formed from a rubber sheath for covering the injection needle 21, wherein the opening 22*a* portion of this protector 22 engages to the exterior portion of the attachment 18*a* of the aforementioned cylindrical tip 18. Instead of the rubber sheath, this protector 22 may be formed from a synthetic resin material, the entire portion of which, or portion corresponding to that surrounding a needle tip 21*t* of the injection needle 21 of which, is transparent, wherein the aforementioned needle tip is sealed in a fluid-tight manner. When using such a structure, a cutting surface 21*a* of the injection needle 21 can be easily detected from outside of the protector 22 by means of the cutting surface detector, in a state with the protector 22 covering the injection needle, as described below.

Figures 12A, 12B:
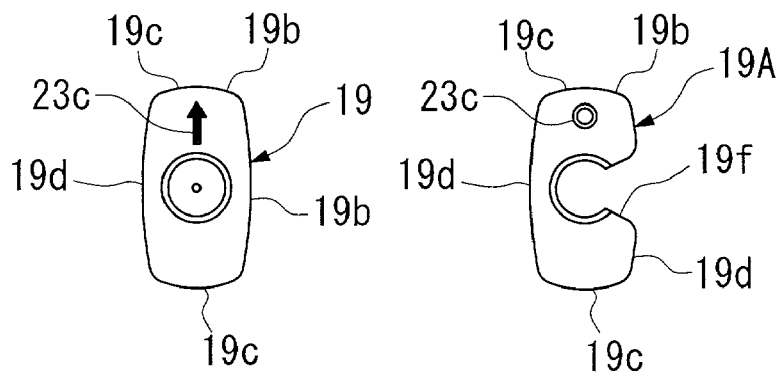
FIGS. 12A and 12B are two examples of directional views of the combined container-syringe shown by Arrow X in FIG. 11.

The aforementioned finger grip 19 is integrated into a single body with a roughly rectangular flange 19*b*, at the posterior end of a cylindrical portion 19*a*, as shown in the axial facing view of FIG. 12A. The aforementioned cylindrical portion 19*a* is engaged to the posterior end of the cylinder 17 in an attachable manner along the axial direction, such that it may rotate around the axis of the cylinder 17. In addition, the aforementioned finger grip 19 is formed from a material such as a synthetic resin, which is elastic and is capable of being sterilized at high temperatures. A thin rib or the like is provided on the attachment (portion) to the cylinder 17, such that the attachment strength is improved by means of imparting an appropriate amount of friction. The finger grip 19 is designed so that it will not unsuspectingly detach.

In addition, as shown in FIG. 12B, in one smooth surface 19*d* side of the flange 19*b*, the opening is sloped facing outward such that the diameter increases therefrom. This opening 19*f* is formed slightly smaller than the inner diameter of the cylindrical member 19*a*, and can serve as a finger grip 19A provided along the axial direction of the flange 19*b* and cylindrical member 19*a*. According to this finger grip 19A, when assembling the syringe body 20, it is also possible to attach the finger grip 19A to the aforementioned cylinder 17 from the axial direction. By means of the aforementioned opening 19*f* it is also possible to easily attach the finger grip 19A to the aforementioned cylinder 17 in a detachable manner from the radial direction thereof.

With regard to the attachment position of the aforementioned finger grip 19, 19A, on the circumference of the cylinder 17, the position of one smooth surface 19*d*, 19*d* (predetermined position on finger grip 19, 19A), lying at right angles with respect to a pair of finger rests 19*c*, 19*c* on flange 19*b*, is set to an angled position that is phase aligned with the position of the cutting surface 21*a* (cutting surface position) of the aforementioned injection needle 21, on the circumference of the cylinder 17 (i.e., such that said cutting surface 21*a* of the aforementioned injection needle 21 and finger grip 19, 19A fall into a predetermined angled positions).

Furthermore, the central aperture of the aforementioned flange 19*d* is formed slightly smaller than the inner diameter of the aforementioned cylinder 17.

As shown in FIG. 11, a scale display 23 which displays the scale and capacity, characters, medication name, and other important information is directly printed or engraved on the exterior portion of the aforementioned cylinder 17. The set position of this scale display 23, on the circumference of the cylinder 17 is aligned with the cutting surface position of the aforementioned injection needle 21 (phase alignment).

Consequently, the three critical components, the cutting surface 21*a* of the injection needle 21, the scale display 23, and the smooth surface 19*d* of the finger grip 19 are in alignment on the circumference of the aforementioned syringe body 20.

Furthermore, it is also possible to alternatively provide the aforementioned scale display 23 in alignment with the position of one finger rest 19*c*, 19*c* of the finger grip 19, 19A (predetermined position on finger grip 19, 19A) according to the request of the physicians and/or nurses. In such cases, the combined container-syringe is designed such that the circumferential position of the aforementioned finger rest 19*c* is aligned with the position of the cutting surface 21*a* of the injection needle 21, such that the three critical components, the cutting surface 21*a* of the injection needle 21, the scale display 23, and the finger rest 19*c* of the finger grip 19 are in alignment on the circumference of the aforementioned syringe body 20.

Figure 13A:
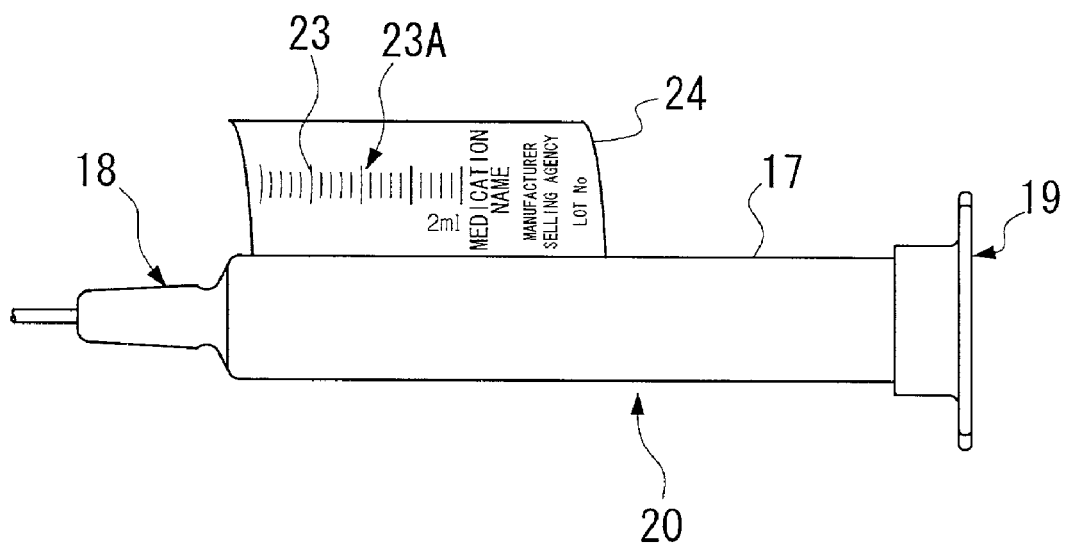
FIGS. 13A and 13B are plane views showing structural examples of the scale, etc. of cylinders.
Figure 13B:
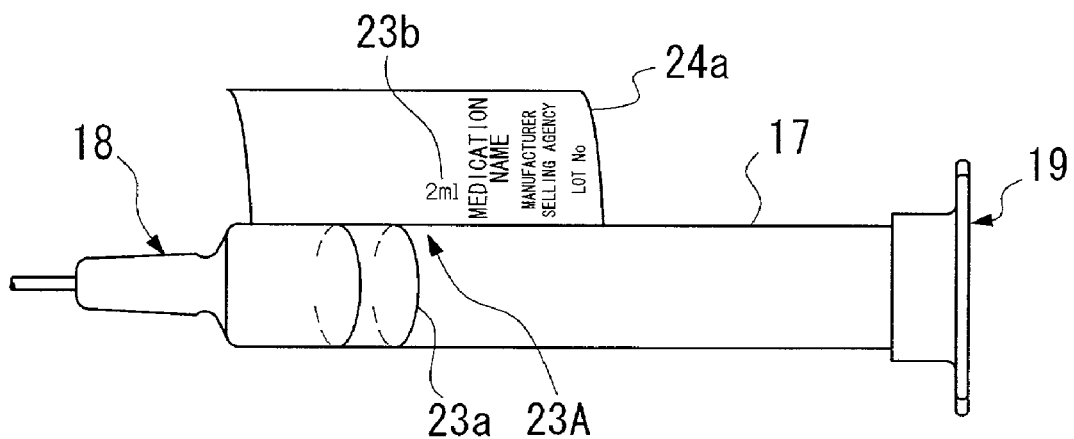

As shown in FIG. 13A, it is also possible to provide the aforementioned scale display 23 on the exterior portion of the cylinder 17, by means of adhering a label 24, onto which this scale display 23 is pre-printed (printed beforehand), onto the exterior portion of the aforementioned cylinder 17. In addition, as shown in FIG. 13B, it is also possible to provide a part of a scale display 23*a* on the aforementioned cylinder 17. Furthermore, the remaining part of the scale display 23*b* may be printed onto a label 24*a* comprising a transparent sheet, and adhered to the exterior surface of the aforementioned cylinder 17, in a manner such that the aforementioned scale display part 23*a* is visible.

The aforementioned scale display 23 and the finger rest 19c can be aligned with the cutting surface position of the injection needle 21, such that they function as a mark 23A indicating the aforementioned cutting surface position. However, this type of the mark 23A can be formed into the shape of the finger grip 19, 19A shown in FIGS. 12A and 12B, or alternatively a mark 23c provided by means of hot stamping, printing, or engraving using a mold, can be adhered to an appropriate and easily visualized location on the finger grip 19, 19A, such that the cutting surface position of the injection needle 21 can be easily confirmed.

Figure 14:
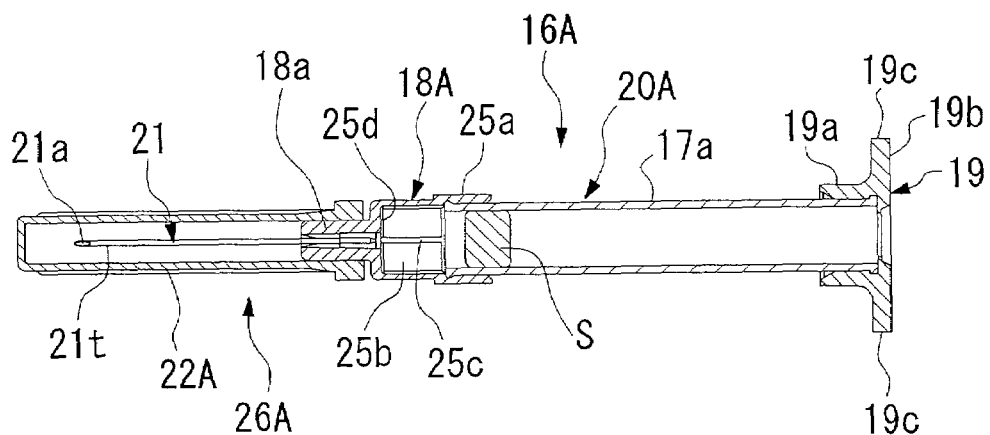
FIG. 14 is a cross-sectional view of a combined container-syringe according to the fifth embodiment of the present invention.

In the following, a combined container-syringe 16A shown in FIG. 14, which utilizes a needle-tube direct attachment system (Duffer system) according to the fifth embodiment of the present invention, will be explained.

In contrast to the aforementioned combined container-syringe 16 in which the cylindrical tip 18 is integrated into a single body with the anterior end of the cylinder 17, in this combined container-syringe 16A, a needle tube of an injection needle 21 is directly attached to the attachment portion of the aforementioned cylindrical tip 18a, which is attachable to the anterior end of the aforementioned cylinder 17a, to form a front assembly 18A. This front assembly 18A is attached to the anterior end of the aforementioned cylinder 17a in a manner allowing both detachment and rotation around the axis of the cylinder 17a. A cap-type protector 22A for covering the injection needle 21 is fitted to the aforementioned cylindrical tip 18a. This protector 22A is formed from a transparent or semi-transparent synthetic resin material, such that the needle tip 21t of the injection needle 21 housed therein can be viewed from the exterior.

The aforementioned front assembly 18A comprises a chamber 25b that accepts a front stopper S, when this front stopper S, manufactured from rubber, moves forward between the attachment portion 25a and cylindrical tip 18a towards the posterior end of the cylinder 17a and is inserted into the anterior end of this cylinder 17a; and a longitudinal groove 25c and a horizontal groove 25d, formed respectively in the interior and exterior of the aforementioned chamber 25b, which allow the passage of a drug within the cylinder 17a to the cylindrical tip 18a.

The remaining structure is identical to that of the aforementioned combined container-syringe 16. The components that are identical those of the aforementioned combined container-syringe 16 are denoted using the same numeral, and their explanations are omitted.

Figure 15:
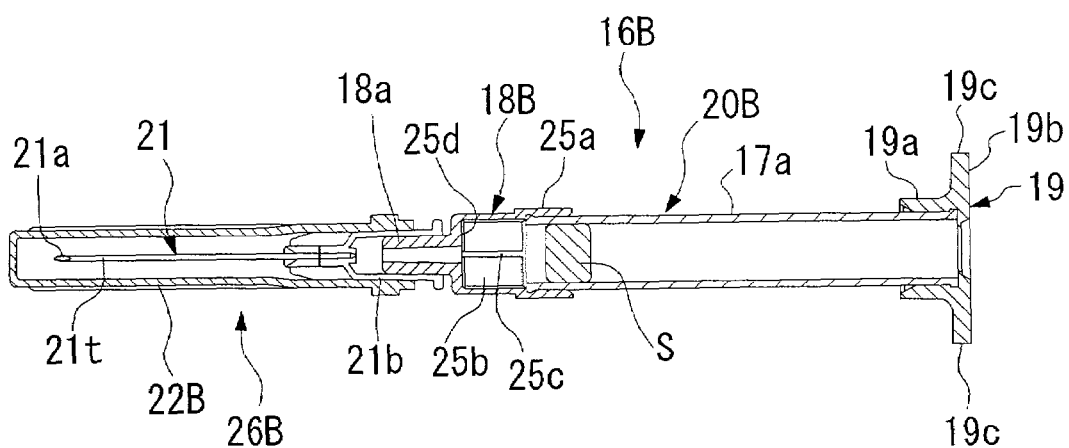
FIG. 15 is a cross-sectional view of a combined container-syringe according to the sixth embodiment of the present invention.

In the following, a combined container-syringe 16B shown in FIG. 15, which utilizes an injection needle attachment system (luer tip system) according to the sixth embodiment of the present invention, will be explained.

In contrast to the aforementioned combined container-syringe 16A in which the injection needle is directly fixed to the attachment of the cylindrical tip 18a of the front assembly 18A, in this combined container-syringe 16B, the cylindrical tip 18a of a front assembly 18B has a luer tip attachment that attaches to the injection needle 21 in a detachable manner via said attachment and a needle base 21b. In addition, this combined container-syringe 16B comprises a protector 22B identical to the cap-type aforementioned protector 22A, which covers the injection needle 21 and fits to the outer aspect of the aforementioned needle base 21b. The remaining structure is identical to that of the aforementioned combined container-syringe 16A. The components that are identical those of the aforementioned combined container-syringe 16A are denoted using the same numeral, and their explanations are omitted.

Figure 16:
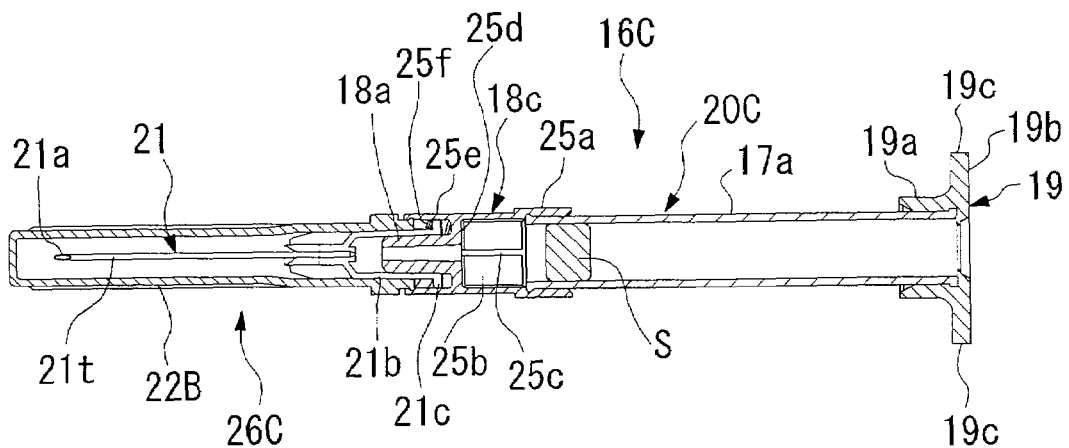
FIG. 16 is a cross-sectional view of a combined container-syringe according to the seventh embodiment of the present invention.

In addition, a combined container-syringe 16C shown in FIG. 16, which utilizes an injection needle attachment system (luer lock system) according to the seventh embodiment of the present invention, will be explained.

Instead of a front assembly 18B possessing a luer tip attachment of the aforementioned combined container-syringe 16B, this combined container-syringe 16C utilizes a front assembly 18C possessing a luer lock attachment. The remaining structure is identical to that of the aforementioned combined container-syringe 16B. The components that are identical those of the aforementioned combined container-syringe 16B are denoted using the same numeral, and their explanations are omitted.

The aforementioned front assembly 18C comprises a luer lock 25e, which serves as the attachment in the luer tip system of the aforementioned front assembly 18B, provided around the exterior of cylindrical tip 18a with a space thereinbetween. An external protrusion 21c at the posterior end of the needle base 21b of the aforementioned injection needle 21 engages with a screw member 25f on the interior aspect of this luer lock 25e. In this manner, loosening of the needle base 21b and careless detachment of the injection needle from the syringe body 20 during use does not occur.

According to the aforementioned combined container-syringe 16, 16A, 16B, 16C, the positions of the cutting surface 21a of the injection needle 21, the scale display 23 of the cylinder 17, 17a, and the smooth surface 19d or the finger rest 19c of the finger grip 19, 19A are in alignment on the circumference of the aforementioned cylinder 17, 17a. As a result, it is possible to efficiently and safely administer an injection without having to perform preparatory operations, such as positional corrections, i.e., to confirm the cutting surface position of the injection needle 21 immediately prior to using the combined container-syringe 16, 16A, 16B, 16C, or aligning a predetermined position of the mark, the finger rest 19c of the finger grip 19, 19A, the scale 23 or the like with the aforementioned cutting surface position.

In the following, the assembly method of assembling the combined container-syringes of the aforementioned fourth through seventh embodiments will be explained with reference to FIGS. 17A~17D.

Figure 17A:
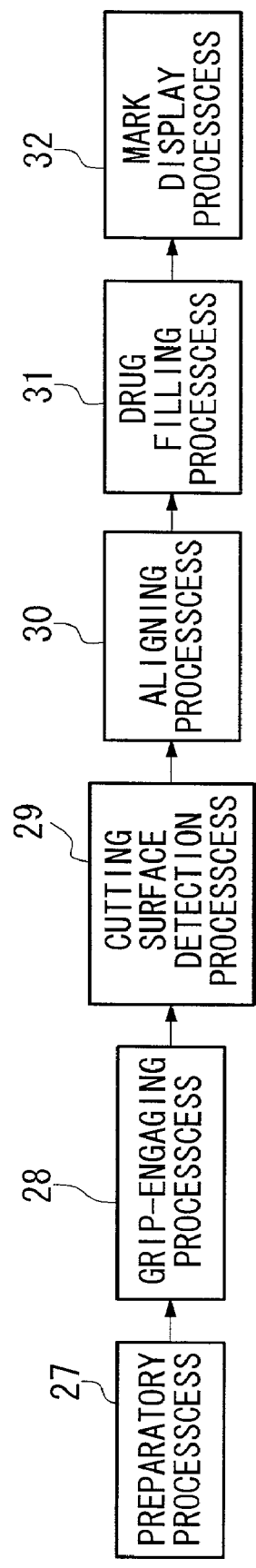

When applying the assembly method of the combined container-syringe according to the fourth embodiment, in assembling the aforementioned combined container-syringe 16, as shown in FIG. 17A, the aforementioned injection needle 21 is directly attached to the cylindrical tip 18 in the preparatory process 27. Subsequently, in the grip-engaging process 28, the finger grip 19 is engaged to the posterior end of the cylinder 17, to which the aforementioned injection needle is attached, with the assembly position (angled position) of either the finger rest 19c or the smooth surface 19d, on the circumference of the cylinder 17, being optionally determined.

Thereafter, in the cutting surface detection process 29, the cylinder 17 is rotated at a low rate around its axis by means of a rotary mechanism, at the positional interface of the assembly unit. A detector (cutting surface detector) utilizing an X-ray camera, CCD camera, laser beam or the like, is also provided on the exterior of the cylinder 17 at the aforementioned positional interface with its detection unit facing towards the center of the cylinder 17 in the radial direction. At this time, the rotation of the cylinder 17 is stopped upon visualizing the needle tip 21t of the aforementioned injection needle 21, and detecting the position of the cutting surface 21a (cutting surface position) on the circumference of the injection needle 21 by means of the aforementioned detector. When the rotation of the aforementioned cylinder 17 is stopped, the cylinder 17 is supported by a base support attached to the aforementioned assembly unit, and positioned to the aforementioned stop position (cutting surface position) on the circumference of the cylinder 17.

In the aforementioned state, during the aligning process 30, the engaging portion of a grip rotary device of the assembly unit is rotated while being lowered, and engaged to the finger grip 19. The aforementioned finger grip 19 is rotated relative to the cylinder 17 at a low speed such that it slips along the circumference of the cylinder 17 resisted by the engaging friction. At this time, the position of the smooth surface 19*d* or the finger rest 19*c*, on the circumference of the cylinder 17, is detected by means of a position detector similar to that used to detect the position of the aforementioned cutting surface. When this aforementioned detected position is aligned with the aforementioned cutting surface position, the grip rotary device stops the rotation of the engaging portion and separates from the finger grip 19.

By establishing the same set position (set phase) for the aforementioned cutting surface detector and the position detector, on the circumference of the cylinder 17, the position of the smooth surface 19*d* or the finger rest 19*c* of the finger grip 19, detected by means of the aforementioned position detector, and the cutting surface position of the injection needle 21 become aligned on the circumference of the cylinder 17 (i.e., the cutting surface 21*a* and the finger grip 19 are assembled at predetermined angled positions). The finger grip 19 then maintains the aforementioned angled position fitted to the cylinder 17 by means of frictional force.

Subsequently, in the drug filling process 31, the syringe body 20 to which the cutting surface 21*a* of the injection needle 21 and finger grip 19 have been attached at predetermined angled positions, is sent to a guard fitting apparatus where the injection needle 21 is covered by a rubber sheath serving as a protector 22. The needle tip 21*t* is then inserted and sealed into the rubber sheath to the tip thereof. As a result, the drug filling the interior of the cylinder 17 is sealed such that leakage from the aforementioned needle tip 21*t* does not occur (guard fitting operation).

Subsequently, the interior of the cylinder 17 is filled with a predetermined amount of a drug, from the finger grip 19 side, by means of a drug filling device (drug filling operation). After filling the aforementioned cylinder 17, an end stopper manufactured from rubber is inserted into the posterior end of the cylinder 17 at the stopper attachment (end stopper insertion operation) to complete the filling operation of the aforementioned drug.

Thereafter, in the mark display process 32, the predetermined angled position of the finger grip 19 is detected by means of a position detector similar to that used to detect the position of the aforementioned cutting surface, and the position of the cutting surface 21*a* of the injection needle 21 is confirmed. By means of a label adhering device, the label 24, onto which the scale display 23 is printed, is then adhered to the exterior of the cylinder 17 on a portion corresponding to the aforementioned angled position at which the cylinder 17 was stopped (label adhering operation). Instead of adhering the label 24 to the aforementioned cylinder 17, it is also possible to provide the scale display 23 by means of directly printing or engraving the aforementioned scale display 23 onto the exterior of the cylinder 17 using an appropriate display unit such as a hot stamp, a laser mark or the like. Furthermore, in addition to the aforementioned scale display 23, it is also possible to provide another mark indicating the cutting surface position of the injection needle 21.

According to the assembly method of the combined container-syringe according to the aforementioned embodiment, it is possible to assemble the combined container-syringe 16 filled with a drug, wherein the positions of the cutting surface 21*a* of the injection needle 21, the smooth surface 19*d* or the finger rest 19*c* of the finger grip 19, and the scale display 23 are correctly aligned, on the circumference of the aforementioned cylinder 17, in single file along the axis of the cylinder 17. Consequently, it is possible to provide the combined container-syringe 16, which can be safely used without the physician or nurse having to correctly re-position the cutting surface of the injection needle 21 or the finger grip 19 just prior to using the combined container-syringe.

Figure 17B:
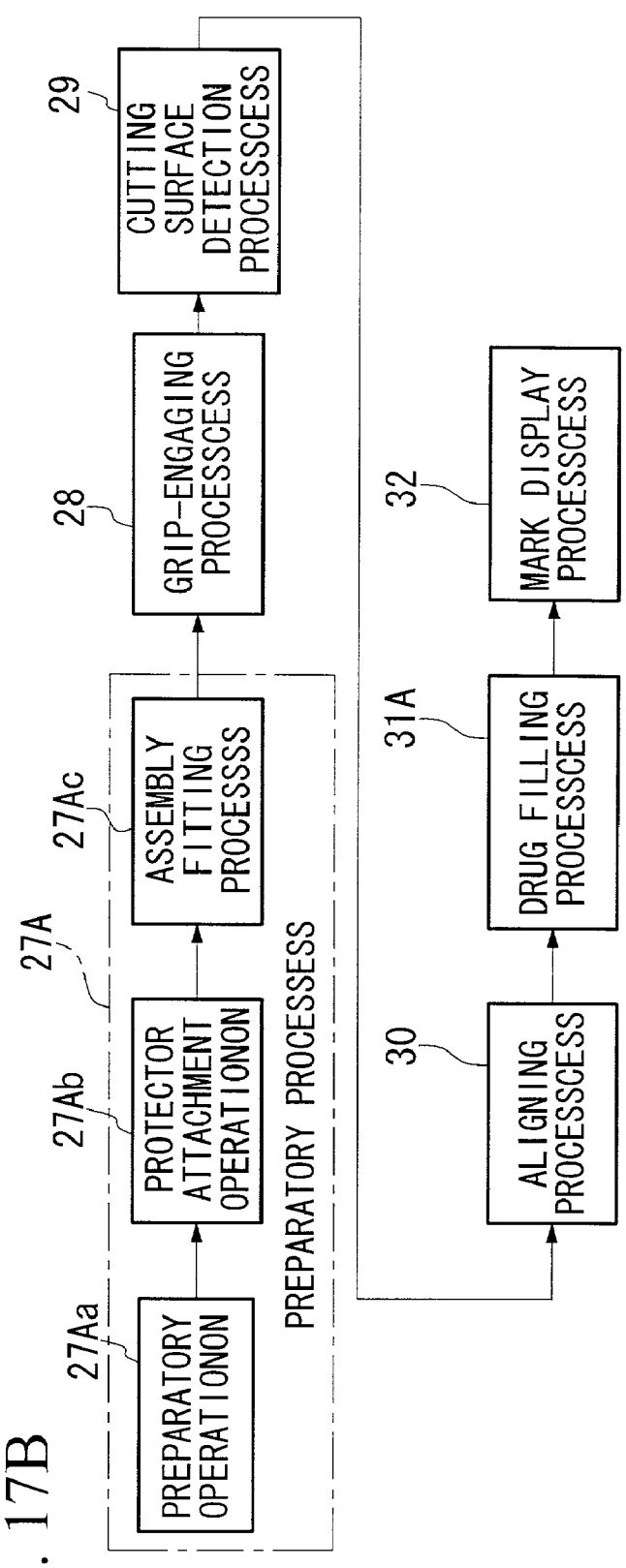

When assembling the combined container-syringe 16A by applying the assembly method of assembling the combined container-syringe according to the fifth embodiment, as shown in FIG. 17B, in the preparatory process 27A, the injection needle 21 is directly attached beforehand to the cylindrical tip 18*a* that is attachable to the anterior end of the cylinder 17, to form the front assembly 18A (preparatory operation 27Aa). Subsequently, the protector 22A is attached to the aforementioned cylindrical tip 18*a* to prepare an injection needle assembly in which the aforementioned injection needle 21 is protected (protector attachment operation 27Ab). The aforementioned injection needle assembly 26A is then fitted to the anterior end of the aforementioned cylinder 17 (assembly fitting operation 27Ac).

In the following, the combined container-syringe 16A is assembled by means of sequentially performing a drug filling process 31A and mark display process 32 after completing the aforementioned grip-engaging process 28, cutting surface detection process 29, and aligning process 30.

In the aforementioned drug filling process 31A, the anterior end of the aforementioned cylinder 17*a* is sealed by means of inserting the front stopper, manufactured from rubber, into the aforementioned the anterior end of the cylinder 17, to which the aforementioned injection needle assembly 26A is fitted (front stopper insertion). The cylinder 17*a* is then filled with a drug.

When assembling a combined container-syringe 16B, 16C by applying the assembly methods for assembling the combined container-syringe according to the sixth and seventh embodiments, as shown in FIG. 17C, in the preparatory process 27B, the injection needle 21 is fitted beforehand to the cylindrical tip 18*a* via the needle base 21*b*, to form the front assembly 18B. Alternatively, the injection needle 21 is attached to the cylindrical tip 18*a* and the luer lock 25*e* by means of the needle base 21*b* and the external protrusion 21*c*, to form the front assembly 18C (preparatory operation 27Ba). Subsequently, the protector 22B is attached to the needle base 21*b* of the aforementioned front assembly 18B or front assembly 18C to prepare the injection needle assembly 26B or 26C (protector attachment operation 27Bb). The aforementioned injection needle assembly 26B or 26C is then fitted to the anterior end of the aforementioned cylinder 2*a* (assembly fitting operation 27Bc).

Thereafter, in the same manner as in the method of the fifth embodiment, the assembly of the combined container-syringe 16B is completed by means of sequentially performing the aforementioned grip-engaging process 28, cutting surface detection process 29, aligning process 30, drug filling process 31A and mark display process 32.

According to the assembly method of the aforementioned combined container-syringe 16A, 16B, and 16C, it is possible to correctly, reliably and easily align the positions of the cutting surface 21a of the injection needle 21, the smooth surface 19d or the finger rest 19c of the finger grip 19, and the scale display 23. Moreover, it is possible to detect the cutting surface position of the injection needle 21 from the exterior, with the protector 22A, 22B attached thereon, and thus the aforementioned assembly can be performed safely and reliably without incurring damage to the injection needle 21.

In the following, the assembly of the aforementioned combined container-syringe, shown in FIG. 17D, is performed using the finger grip 19A shown in FIG. 12B. In the preparatory process 27C, the same operations 27Ca, 27Cb, 27Cc as in the aforementioned preparatory process 27A or 27B are performed. In this manner, the aforementioned front assembly, in which the injection needle covered by the protector is fitted to the cylindrical tip, is attached to the anterior end of the aforementioned cylinder. After performing the drug filling process 31A in the assembly method according to the aforementioned fifth and sixth embodiments, the aforementioned grip-engaging process 28A, cutting surface detection process 29, aligning process 30, and mark display process 32 are sequentially performed to complete the assembly of the combined container-syringe.

The grip-engaging process 28A differs from the aforementioned grip-engaging process 28, in which the aforementioned finger grip 19 is engaged to the posterior end of the cylinder 17a from an axial direction, only in that the finger grip 19A is engaged to the aforementioned cylinder 17a from a radial direction.

According to this assembly method of assembling the combined container-syringe, it is possible to provide an interchangeable assembly process, wherein depending on the circumstances at the time of the assembly process, a drug can first be filled into the interior of the cylinder 17a followed by assembly of the plunger, and then attachment of the finger grip 19A.

Furthermore, in the aforementioned assembly method of the combined container-syringe, the mark display process 32 is performed after conducting the drug filling process 31, 31A, 31B. However, the aforementioned assembly method is not limited thereto, and the order can be reversed, or alternatively the drug filling process 31, 31A, 31B can be removed from the assembly process, and conducted separately.

Figure 18:
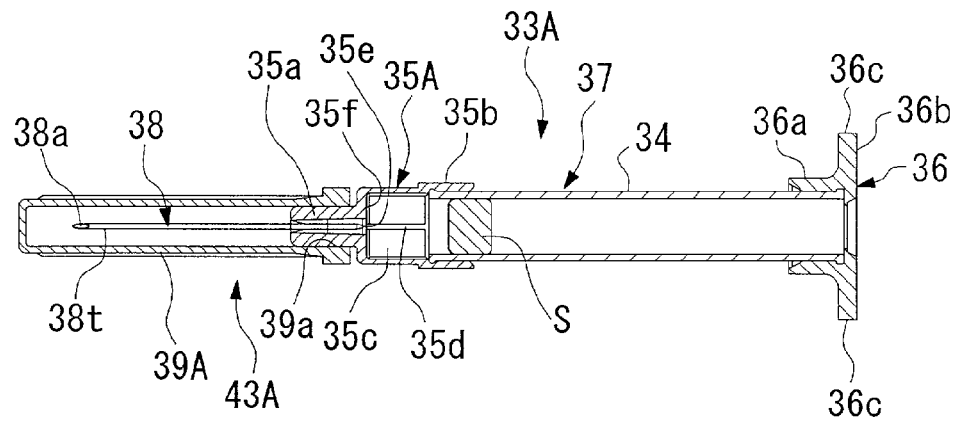
FIG. 18 is a cross-sectional view of a combined container-syringe according to the eighth embodiment of the present invention.

FIGS. 18 to 20 show a combined container-syringe 33A which utilizes a needle-tube direct attachment system according to the eighth embodiment of the present invention.

This combined container-syringe 33A comprises a syringe body 5, containing a cylindrical-shaped cylinder 34 provided with a cylindrical tip 35A at the anterior end thereof, and a plunger; a finger grip 36 provided at the posterior end of the cylinder 34; an injection needle 38 fitted with a needle-tube base which is directly attached to an attachment 35a provided at the anterior end of the aforementioned cylindrical tip 35A; and a cap-type protector 39A for covering the injection needle 38, the opening portion 39a of which is engaged to the exterior portion of the aforementioned attachment 35a of the aforementioned cylindrical tip 35A. The aforementioned protector 39A is manufactured using a transparent or semi-transparent synthetic resin material, such that the needle tip 38t of the aforementioned injection needle 38 therein is visible from the exterior.

The aforementioned cylindrical tip 35A is provided with a cylindrical-shaped engaging member 35b at the posterior end thereof which engages to the anterior end of the cylinder 34, in a manner allowing rotation around the axis of the cylinder 34; this cylindrical-shaped engaging member 35b is also attachable in the axial direction. An inner chamber (bypass chamber) 35c is provided in between the aforementioned attachment 35a and the engaging member 35b of the cylindrical tip 35A. This inner chamber 35c receives a front stopper S at the time when said front stopper S, which is manufactured from rubber and inserted into the anterior end of the cylinder 34, is moved forward. In addition, this aforementioned inner chamber 35c possesses an inner diameter that is slightly larger than the outer diameter of the aforementioned front stopper S. Furthermore, this inner chamber 35c respectively comprises at least one longitudinal bypass groove 35d, provided in the inner wall thereof, which runs parallel to the axial direction; and a horizontal bypass groove 35f, provided in the bottom portion thereof, which connects the aforementioned longitudinal bypass groove 35d and a small aperture 35e, which connects to the attachment 35a side of the injection needle 38.

Figure 19A:
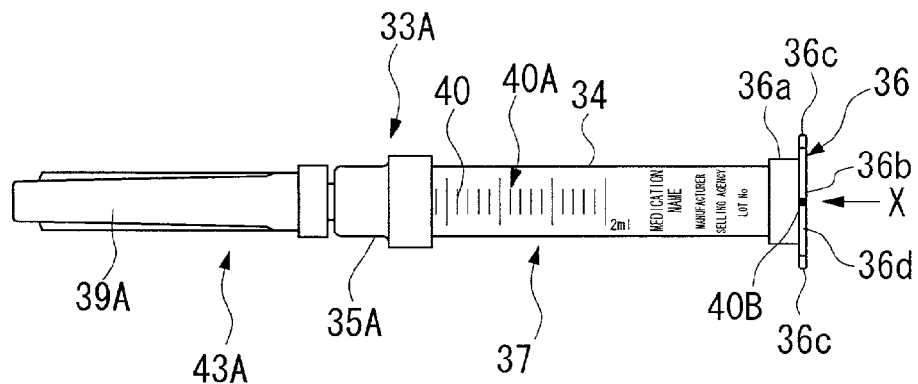
FIGS. 19A and 19B are two examples of plane views of the combined container-syringe.

As shown in FIGS. 18, 19A, and 20A, the aforementioned finger grip 36 comprises a cylindrical member 36a which engages to the posterior end of the cylinder 34; and a roughly rectangular flange 36b (when viewed from the front), which is integrated with the cylindrical member 36a into a single body. In addition, the aforementioned finger grip 36 is formed from material such as a synthetic resin, which is elastic and is capable of being sterilized at high temperatures. A thin rib or the like is provided on the attachment (portion) to the cylinder 34, such that the attachment strength is improved by means of imparting an appropriate amount of friction.

The engagement position of the finger grip 36 on the circumference of the cylinder 34 is set to an angled position where the position (predetermined position on the finger grip 36) of one smooth surface 36d, 36d lying at right angles to a pair of finger rests 36c, 36c of the flange 36b is aligned with the position of the cutting surface 38a (cutting surface position) of the aforementioned injection needle 38 (i.e., such that the cutting surface 38a of the aforementioned injection needle 38 and the finger grip 36 move into predetermined positions) on the circumference of the cylinder 34. Furthermore, the center portion of the flange 36b is formed slightly smaller than the inner diameter of the aforementioned cylinder 34.

Figure 19B:
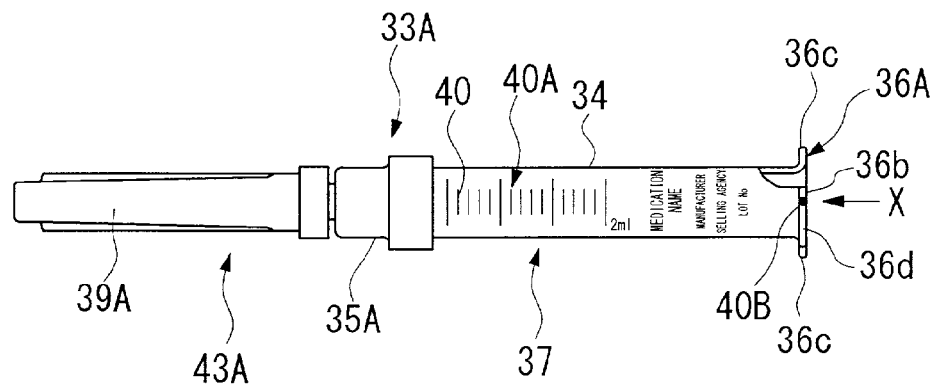

Furthermore, with regard to the aforementioned finger grip, instead of providing the finger grip 36 which engages the aforementioned cylinder 34, it is also possible to provide a finger grip 36A which is formed into a single body with the cylinder 34, as shown in FIGS. 19B and 20B. In such cases, the position of one smooth surface 36d, 36d lying at right angles to a pair of finger rests 36c, 36c of the flange 36b is set to an angled position in which it is aligned with the position of the cutting surface 38a of the aforementioned injection needle 38 on the circumference of the cylinder 34. The aforementioned finger grip 36, 36A comprises a pair of a smooth surfaces 36d, 36d, and is formed into a rectangular shape to prevent the rotation of the syringe body 37.

As shown in FIGS. 19A and 19B, a scale display 40 which displays numbers indicating the scale and capacity, characters, medication name, and other vital information, is provided either directly printed or engraved on the exterior surface of the aforementioned cylinder 34. The set position on the circumference of the cylinder 34 of the aforementioned scale display 40 is aligned with the cutting surface position of the aforementioned injection needle 38 (phase aligned).

Consequently, the three critical components, the cutting surface 38a of the injection needle 38, the scale display 40, and the smooth surface 36d of the finger grip 36, 36A are in alignment on the circumference of the cylinder 34.

Furthermore, it is also possible to alternatively provide the aforementioned scale display 40 in alignment with the position of one finger rest 36c, 36c of the finger grip 36, 36A (predetermined position on the finger grip 36, 36A). In such cases, the position of the cutting surface 38a of the injection needle 38 is aligned with the position of the aforementioned finger rest 36c, such that the three critical components, the cutting surface 38a of the injection needle 38, the scale display 40, and the finger rest 36c of the finger grip 36 are in alignment on the circumference of the aforementioned syringe body 37.

In addition, the aforementioned scale display 40 may alternatively be provided by means of adhering a label 41, onto which the aforementioned scale display 40 has been printed beforehand, onto the exterior of the aforementioned cylinder 34, as shown in FIG. 21A. In addition, it is also possible to provide part of a scale display 40a on the aforementioned cylinder 34, as shown in FIG. 21B. Furthermore, the remaining part of the scale display 40b may be printed onto a label 41a comprising a transparent sheet, and adhered to the exterior surface of the aforementioned cylinder 34 in a manner such that the aforementioned scale display part 40a is visible.

The aforementioned scale display 40 and the finger rest 36c can be aligned with the cutting surface position of the injection needle 38, such that they function as a mark 40A indicating the aforementioned cutting surface position. In addition, a mark 40B, may also be provided separately at a central location on the circumference of the aforementioned finger rest 36c, 36c, or the smooth surface 36d, 36d, or alternatively provided on a single location on the end face of the flange 36b, by means of hot stamping, printing, or engraving using a mold. By means of providing such the mark 40B, the cutting surface position of the injection needle 38 can be easily confirmed, and the positions of the finger rest 36c and/or the smooth surface 36d can be reliably detected by the detector at the time of assembling the combined container-syringe 33A described below.

In the combined container-syringe 33A comprising the aforementioned construction, a plunger (not shown in the figures) is inserted into the back portion of the cylinder 34 in a manner allowing it to slide in the axial direction of the cylinder 34. A drug is filled into the interior of the cylinder 34, between the aforementioned plunger and front stopper S, and sealed therein. During usage, when a plunger rod connecting to the aforementioned plunger is pressed forward, both the aforementioned drug and front stopper S move forward from the cylinder 34, and enter the inner chamber 35c of the aforementioned cylindrical tip 35A. As a result, the seal holding the drug in the cylinder 34 via the front stopper S is released, and the drug is introduced into the injection needle 38 from a small aperture 35e of the attachment 35a on the aforementioned front assembly 35, passing through the longitudinal bypass groove 35d and the horizontal bypass groove 35f of the aforementioned inner chamber 35c.

Furthermore, in the aforementioned combined container-syringe 33A, with regard to the external shape and dimensions of the anterior end of the cylinder 34, the material of the cylindrical tip 35A fitted to the aforementioned, and the external shape and dimensions of the engaging member of the cylindrical tip 35A, must be set to allow for keeping the aforementioned engaging member completely fluid and airtight, in order so that during usage, the drug does not leak to the exterior while increasing the pressure by pressing the aforementioned plunger rod, and so that bacteria and the like do not penetrate the interior by passing through the aforementioned engaging member. Moreover, prior to filling of the drug, after the aforementioned combined container-syringe 33A is heat sterilized to approximately 120° C. by means of an high-pressure steam sterilizing unit, the combined container-syringe 33A is further subjected to high temperatures for a substantial period of time in the subsequent drying process.

Therefore, the aforementioned front assembly 35 is preferably manufactured from a material having a satisfactory heat resistance for the high-pressure steam sterilization, an appropriate elasticity for engaging the aforementioned cylinder 34 in a fluid and airtight manner, and a transparency enough that the nature of the drug passing through the interior and "flash back" of blood can be visualized. Examples of such appropriate materials include polypropylene, poly-4-methylpentene (TPX) and the like.

Figure 22:
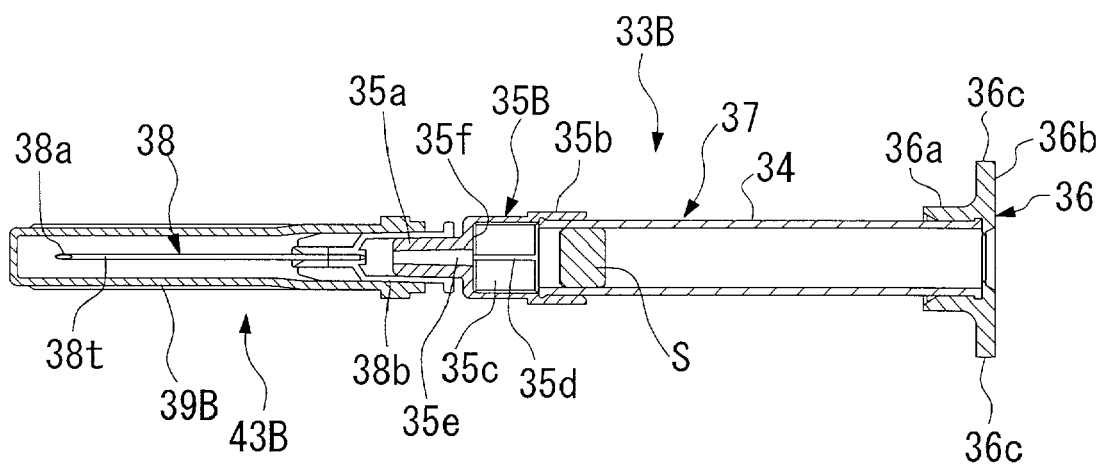
FIG. 22 is a cross-sectional view of a combined container-syringe according to the ninth embodiment of the present invention.

FIG. 22 shows a combined container-syringe 33B which utilizes an injection needle attachment system (luer tip system) according to the ninth embodiment of the present invention.

In contrast to the aforementioned combined container-syringe 33A in which the injection needle 38 is directly fixed to the attachment 35a of the cylindrical tip 35A, in this combined container-syringe 33B, a cylindrical tip 35B utilizes a luer tip system for the attachment 35a. In this system, the injection needle 38 is attached to this attachment 35a in a detachable manner via a needle base 38b. A cap-type protector 39B identical to the aforementioned protector 39A for covering the injection needle 38 is engaged to the exterior portion of the aforementioned needle base 38b. The remaining structures are identical to those of the aforementioned combined container-syringe 33A; these components that are identical those of the aforementioned combined container-syringe 33A are denoted using the same numeral, and their explanations are omitted.

Figure 23:
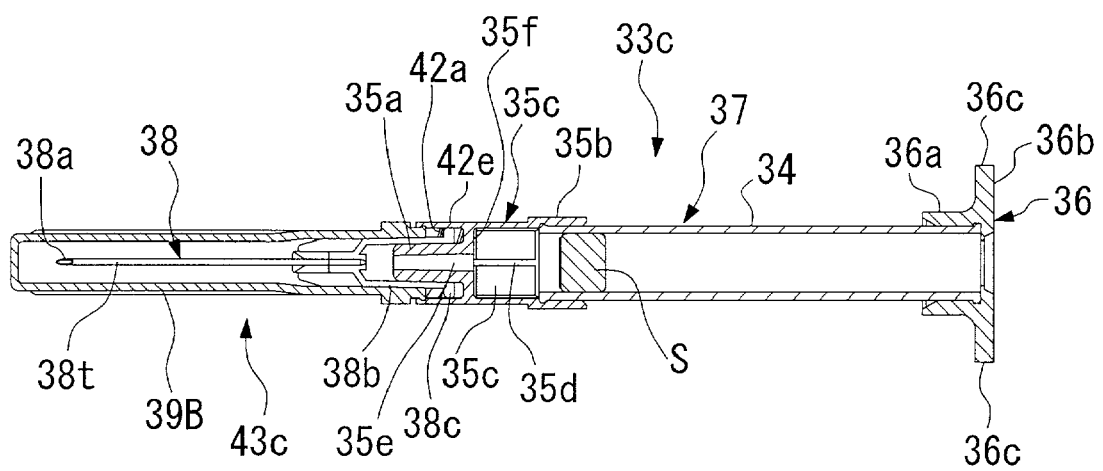
FIG. 23 is a cross-sectional view of a combined container-syringe according to the tenth embodiment of the present invention.

FIG. 23 shows a combined container-syringe 33C which utilizes an injection needle attachment system (luer lock system) according to the tenth embodiment of the present invention.

Instead of comprising a cylindrical tip 35B possessing the luer tip attachment of the aforementioned combined container-syringe 33B, this combined container-syringe 33C comprises a cylindrical tip 35C possessing an attachment which utilizes a luer lock system. The remaining structures are identical to those of the aforementioned combined container-syringe 33B; these components that are identical those of the aforementioned combined container-syringe 33B are denoted using the same numeral, and their explanations are omitted.

The aforementioned cylindrical tip 35C comprises a luer lock 42 provided with a space in between it and the exterior of the attachment 35a which utilizes the luer tip system on the aforementioned cylindrical tip 35B. An external protrusion 38, provided at the posterior end of the needle base 38b of the aforementioned injection needle 38, engages a screw member 42a on the interior aspect of the aforementioned luer lock 42. In this manner, loosening of the needle base 38b and careless detachment of the injection needle 38 from the cylinder 34 during use does not occur.

In addition, instead of the aforementioned finger grip 36, in the same manner as the combined container-syringe 33A, the aforementioned combined container-syringe 33B, 33C may also comprise a finger grip 36A that is integrated into a single body with the cylinder 34, as shown in FIG. 19B.

According to the aforementioned combined container-syringes 33A, 33B, 33C, the three critical components, the cutting surface 38a of the injection needle 38, the scale display 40 of the syringe body 37, and the smooth surface 36d or the finger rest 36c of the finger grip 36A can be aligned correctly on the circumference of the aforementioned syringe body 37. As a result, when using the combined container-syringe 33A, under no circumstance must the combined container-syringe be used in a state in which the position of the scale display, the finger rest, and the like are not aligned. In addition, when using the combined container-syringes 33B, 33C, it is possible to efficiently and safely administer an injection without having to perform preparatory operations, such as positional corrections (i.e., confirming the cutting surface position of the injection needle 38 immediately prior to use, or aligning the predetermined position of the finger rest 36c of the finger grip 36, 36A, the scale display 40 or the like with the aforementioned cutting surface position).

Moreover, it is possible to further increase the safety of the aforementioned combined container-syringe by means of providing the mark 40B on the smooth surface 36d or the finger rest 36c of the finger grip 36, 36A, or the end face of the flange 36b, such that the cutting surface position of the injection needle 38 can be clearly identified.

In the following, the assembly methods for assembling the aforementioned combined container-syringes 33A, 33B, 33C will be explained with reference to FIG. 24.

Figure 24:
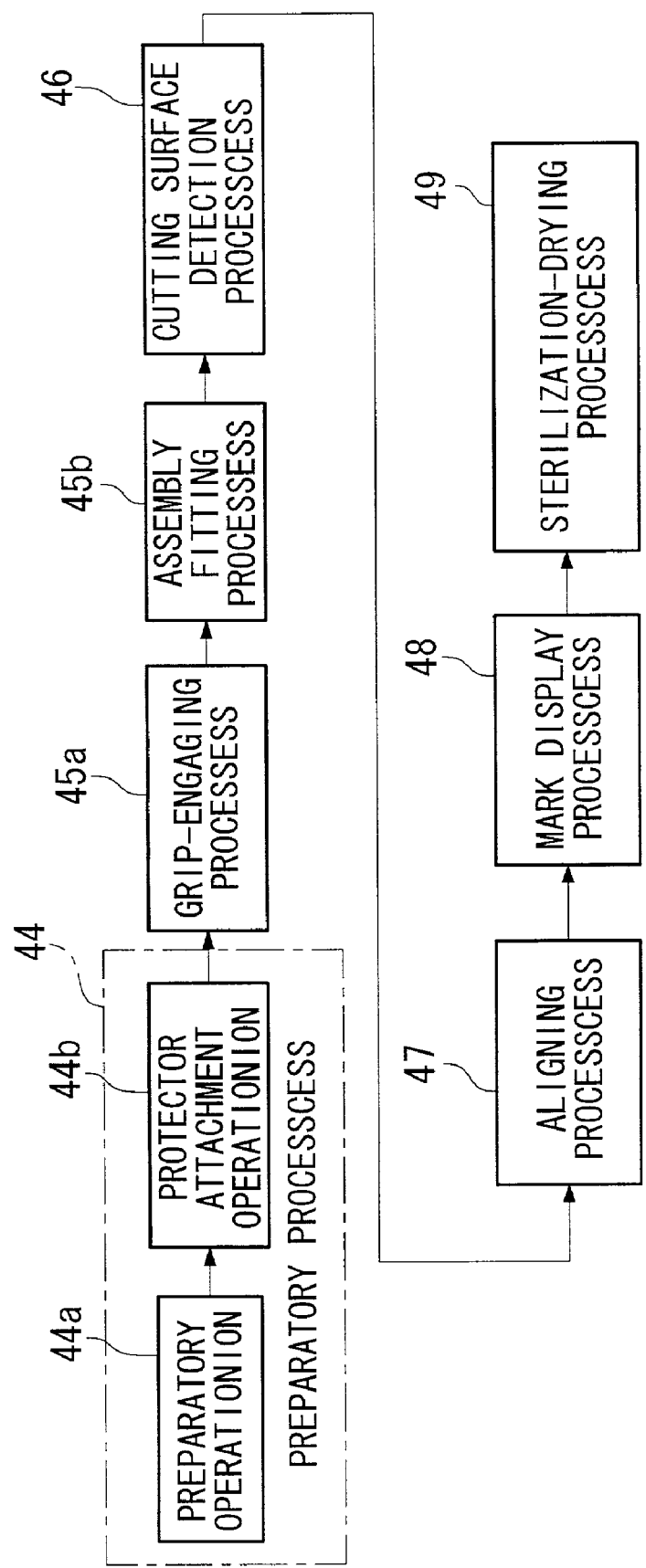
FIG. 24 is a diagram showing the assembly process of a method of assembling a combined container-syringe according an eighth embodiment of the present invention.

In the assembly method of the combined container-syringe 33A according to the eighth embodiment of the present invention, as shown in FIG. 24, the aforementioned injection needle 38 is first directly attached to the attachment 35a of the cylindrical tip 35A, in the preparatory process 44, to form a front assembly (front assembly preparatory process 44a). Subsequently, the protector 39A is attached to the aforementioned attachment 35a to prepare the injection needle assembly 43A in which the aforementioned injection needle 38 is protected (protector attachment operation 44b).

Subsequently, in the case of an engaging-type finger grip, the finger grip 36 is engaged to the posterior end of the aforementioned cylinder 34 (grip-engaging process 45a).

Thereafter, in the assembly fitting process 45b, the cylinder 34 and the injection needle assembly 43A prepared in preparatory process 44 (including front assembly preparatory process 44a and protector attachment operation 44b) are first transported into the assembly unit. The cylinder 34 is then fitted to the cylindrical tip 35A of the aforementioned injection needle assembly 43A, at the assembly attachment portion of the assembly unit, in a fluid and airtight manner allowing for rotation around the circumference of the cylinder 34. In this construction, the assembly position (angled position), on the circumference of the cylinder 34, of either the finger rest 36c or the smooth surface 36d of the finger grip 36, provided on the aforementioned cylinder 34, is randomly determined.

Furthermore, depending on the circumstances at the time of assembly, it is also possible to perform the aforementioned grip-engaging process 45a and assembly fitting process 45b at the same time.

Thereafter, in cutting surface detection process 46, the cylinder 34 is rotated at a low rate around its axis by means of a rotary mechanism, at the positional interface of the assembly unit via the finger grip 36. A detector (cutting surface detector) utilizing an X-ray camera, CCD camera, laser beam or the like, is also provided on the exterior of the cylinder 34 at the aforementioned positional interface with its detection unit facing towards the center of the cylinder 34 in the radial direction. At this time, the rotation of the cylinder 34 is immediately stopped upon visualizing the needle tip 38t of the aforementioned injection needle 38 and detecting the position of the cutting surface 38a (cutting surface position) on the circumference of the injection needle 38 by means of the aforementioned detector. When the rotation of the aforementioned cylinder 34 is stopped, the cylindrical tip 35A is supported by a base support attached to the aforementioned assembly unit, and positioned to the aforementioned stop position (cutting surface position) on the circumference of the cylindrical tip 35A.

In the aforementioned state, during aligning process 47, the engaging portion of a grip rotary device of the assembly unit is rotated while being lowered, and engaged to the finger grip 36. The aforementioned finger grip 36 is rotated relative to the cylinder 34 at a low speed such that it slips relative to the cylindrical tip 35A along the circumference of this cylinder 34, resisted by the engaging friction between the aforementioned cylindrical tip 35A and the cylinder 34. At this time, the position of the smooth surface 36d or the finger rest 36c, on the circumference of the cylinder 34, is detected by means of a position detector similar to that used to detect the position of the aforementioned cutting surface. When this aforementioned detected position is aligned with the aforementioned cutting surface position, the grip rotary device stops the rotation of the engaging portion and separates from the finger grip 36.

At the time of detecting the position of the aforementioned finger grip 36, by means of providing the mark 40B on the smooth surface 36d or the finger rest 36c of the finger grip 36, 36A, or the end face of the flange 36b, it is possible to precisely conduct the aforementioned position detection using a position detector.

By establishing the same set position (set phase) for the aforementioned cutting surface detector and position detector, on the circumference of the cylinder 34, the position of the smooth surface 36d or the finger rest 36c of the finger grip 36, detected by means of the aforementioned position detector, and the cutting surface position of the injection needle 28 become aligned on the circumference of the cylinder 34 (i.e., the cutting surface 38a and finger grip 36 are assembled at predetermined angled positions). The cylindrical tip 35A then maintains the aforementioned angled position fitted to the cylinder 34 by means of frictional force.

Thereafter, in the mark display process 48, the predetermined angled position of the finger grip 36 is detected by means of a position detector similar to that used to detect the position of the aforementioned cutting surface, using the aforementioned smooth surface 36d, finger rest 36c or mark 40B, and the position of the cutting surface 38a of the injection needle 38 is confirmed. By means of a label adhering device, the label 41, onto which the scale display 40 is printed, is then adhered to the exterior of the cylinder 34 on a portion corresponding to the aforementioned angled position at which the cylinder 34 was stopped (label adhering operation). Instead of adhering the label 41 to the aforementioned cylinder 34, it is also possible to provide the scale display 40 by means of directly printing or engraving the aforementioned onto the exterior of the cylinder 34 using an appropriate display unit such as a hot stamp, laser marker or the like (scale display formation).

After the aforementioned mark display process 48, the combined container-syringe 33A is heat sterilized to a high temperature of approximately 120° C. by means of an high-pressure steam sterilizing unit for only a predetermined period of time, and then returned to room temperature during the drying process (sterilization-drying process 49). In this sterilization-drying process 49, the cylindrical tip 35A fitted to the aforementioned cylinder 34 comprises a specific synthetic resin material, and thus contracts slightly from the temperature change during the aforementioned heating and cooling. As a result, the fitting portion (attachment) of the cylindrical tip 35A to the cylinder 34 tightens, such that during the subsequent drug filling or packaging processes, the aforementioned cylindrical tip 35A neither loosens nor easily rotates with respect to the cylinder 34.

The aforementioned sterilization-drying process 49 includes a steam sterilizing process in which the aforementioned combined container-syringe 33A is sterilized using high-pressure steam. However, instead of this steam sterilizing process, it is also possible to perform the sterilization process using a chemical, light ray irradiation or the like.

According to the assembly method of assembling the combined container-syringe according to the aforementioned eighth embodiment, it is possible to reliably assemble the combined container-syringe 33A, wherein the critical components, the cutting surface 38a of the injection needle 38, the smooth surface 36d or the finger rest 36c of the finger grip 36 are aligned correctly on the circumference of the aforementioned syringe body 37 in single file along the axis of the cylinder 34. Consequently, it is possible to provide the combined container-syringe 33, which can be safely used without the physician or nurse having to correctly re-position the cutting surface of the injection needle 38 or the finger grip 36 immediately prior to the injection.

Moreover, since the aforementioned protector 39A comprises a transparent or semi-transparent material, it is possible to detect the cutting surface position of the injection needle 38 from the exterior, with the protector 39A attached to the cylindrical tip 35A. As a result, this cylindrical tip 35A can be handled as the injection needle assembly 43A wherein the injection needle 38 is protected by the aforementioned protector 39A, such that it is possible to perform the aforementioned assembly in a safe and reliable manner, without incurring damage to the injection needle 38.

In the assembly method for assembling the combined container-syringe 33B or 33C, in the preparatory operation 44a of the aforementioned preparatory process 44, instead of using the cylindrical tip 35A comprising the attachment 35a to which the injection needle 38 is directly attached, the cylindrical tip 35B comprising the luer tip to which the injection needle 38 is attached via the needle base 38b, or the cylindrical tip 35C comprising the luer tip and the luer lock 42e to which the injection needle 38 is attached via the needle base 38b and the external protrusion 38c is used. In addition, in the aforementioned protector attachment operation 44b, instead of assembling the injection needle assembly 43A in which the front assembly is attached to the protector 39A, the injection needle assembly 43B or 43C is used, in which the front assembly is attached to the protector 39B.

The remaining processes, the grip-engaging process 45a, assembly fitting process 45b, cutting surface detection process 46, aligning process 47, mark display process 48, and sterilization-drying process 49 are sequentially performed in the same manner as in the method of the aforementioned eighth embodiment to complete the assembly of the combined container-syringe 33B or 33C.

The assembly method of assembling the combined container-syringe 33B, 33C achieves the same effects and results as the assembly method of assembling a combined container-syringe 33A.

Furthermore, in the assembly methods for assembling the combined container-syringe according to aforementioned eighth through tenth embodiments, when necessary, a drug filling process may be provided after the aforementioned sterilization-drying process 49.

In the aforementioned drug filling process, the anterior end of the aforementioned cylinder 34 is sealed by means of inserting the sterile rubber front stopper S into the aforementioned the anterior end of the sterilized and dried cylinder 34 (at the stopper attachment), to which the cylindrical tip 35A, 35B, 35C is fitted (front stopper insertion). The cylinder 34 is then filled from the finger grip 36, 36A side with a predetermined amount of a drug using a drug filling apparatus (drug filling operation). The drug filling process is then completed by means of inserting a sterile rubber end stopper into the posterior end of the cylinder 34 at the stopper attachment (end stopper insertion).

For the sake of safety, is also possible to perform an additional steam sterilization of the combined container-syringe after the aforementioned drug filling process. In addition, it is also possible to insert the front stopper S into the cylinder 34 and sterilize the aforementioned after the grip-engaging process 45a or assembly fitting process 45b.

As described in the aforementioned, by means of the assembly method of assembling the combined container-syringe according to the present invention, it is possible to provide the combined container-syringe, in which the positions of the cutting surface of the injection needle, the scale display and/or the finger grip are aligned in a single direction. As a result, it is possible to provide the combined container-syringe, which can be safely used without the physician or nurse having to correctly re-position the injection needle just prior to use.

In addition, in the case when the scale display of the cylinder is provided by means of adhering the label displaying the aforementioned scale display onto the exterior of the cylinder, after the mark display process, it is possible to shift the sequence of the process of fitting the injection needle assembly to the cylindrical tip, and the process of adhering the aforementioned label to the exterior of the cylinder (depending on the circumstances of the combined container-syringe assembly process).

In addition, in the case when the finger grip is engaged to the cylinder in a manner allowing rotation around the cylinder axis, such that the position of the finger rest of the finger grip can be adjusted on the circumference of the cylinder, the process of adjusting the position of the aforementioned finger rest to a predetermined position may be optionally conducted either before or after the process of fitting the aforementioned injection needle assembly to the cylindrical tip, depending on the circumstances of the combined container-syringe assembly process.

In addition, according to the combined container-syringe provided with the attachment which utilizes the direct attachment system, luer tip system, or luer lock system, the aforementioned injection needle can be reliably attached to the cylinder. As a result, the cutting surface position of the injection needle can be correctly aligned with the position of the scale display and/or finger grip, such that the aforementioned assembly can be reliably and easily performed.

In the assembly method of assembling the combined container-syringe by means of detecting the cutting surface position of the injection needle, and directly aligning this cutting surface position with the position of the scale display, it is possible to not only correctly align the aforementioned cutting surface position of the injection needle and the position of the scale display in a single direction, but also omit the mark display process with respect to the injection assembly. Consequently, the assembly process can be further simplified, and the assembly of the combined container-syringe can be conducted in a highly efficient manner.

In addition, with respect to the assembly method in which the mark, displaying the cutting surface position on the circumference of the injection needle, is provided on either the exterior portion of the injection needle assembly in which the protector is fitted over the injection needle, or the finger grip, during the assembly process, it is possible to correctly align the aforementioned cutting surface position of the injection needle and the position of the scale display on the circumference of the cylinder. Additionally, when using the combined container-syringe assembled according to the aforementioned assembly method, if by chance the positions of the scale display and mark provided on the aforementioned injection needle assembly or finger grip are inappropriately aligned on the circumference of the cylinder, it is possible for the user to readily observe this error, and then easily re-position either the injection needle or finger grip.

Consequently, it is possible to reliably avoid using a combined container-syringe in which the cutting surface of the injection needle and finger rest of the finger grip of the syringe body are positioned inappropriately with respect to each other, which in turn avoids rendering an unsafe or difficult injection.

In addition, even when the cylindrical tip comprises a hub luer lock that is shaped to allow attachment to the cylinder, by means of providing the aforementioned mark on the exterior surface of the hub luer lock, it is possible to provide a combined container-syringe in which the positions of aforementioned cutting surface of the injection needle and scale display of the cylinder are correctly aligned on the circumference of the cylinder.

In addition, the assembly method in which the cutting surface position is exhibited, by means of adhering a label displaying a scale or the like onto the exterior of the cylinder, renders a printing device unnecessary in the assembly unit. Thus, the scale display, which serves as a mark indicating the position of the injection needle, can be easily and quickly provided on the exterior of the cylinder.

In addition, according to the assembly method in which a drug filling process is provided in between the aforementioned aligning process and mark display process, it is possible to easily provide a combined container-syringe in which the cylinder of the syringe body is filled with a drug.

In addition, according to a combined container-syringe in which the finger grip is provided with an opening in the radial direction, depending on the circumstances of the assembly process, after filling the aforementioned cylinder interior with a drug and inserting the plunger into the cylinder, it is possible to engage the finger grip to the cylinder from the radial direction by means of this aforementioned opening.

In addition, according to the assembly method in which a protector is fitted over the injection needle, and the cutting surface of the injection needle is detected from outside the protector, it is possible to safely and reliably perform the assembly operation without causing damage to the injection needle (during the assembly process).

Lastly, according to the assembly method in which steam sterilization is performed using a cylindrical tip comprising polypropylene or poly-4-methylpentene, when cooling the front assembly that has been heated in the steam sterilization process, the attachment of the aforementioned front assembly contracts an appropriate amount due to the temperature change, thereby tightening the attachment to the aforementioned cylinder. As a result, it is possible for a user to safely use the combined container-syringe without unsuspected rotation of the aforementioned attachment.

What is claimed is:

1. A combined container-syringe comprising a syringe body containing a cylindrical-shaped cylinder; a cylindrical tip provided at an anterior end of the cylinder; a finger grip provided at a posterior end of said cylinder; an injection needle fitted to said cylindrical tip; and a protector covering said injection needle; wherein, a mark indicating a position of a cutting surface on a circumference of said injection needle is provided on each exterior surface of an attachment of said injection needle for fitting said injection needle to said cylindrical tip, and said protector; and a position of said mark and a position of a scale display, provided on an exterior portion of said cylinder, are in alignment on a circumference of said cylinder.

2. A combined container-syringe comprising a syringe body containing a cylindrical-shaped cylinder; a cylindrical tip provided at an anterior end of the cylinder; a finger grip provided at a posterior end of said cylinder; an injection needle fitted to said cylindrical tip; and a protector covering said injection needle, wherein said cylindrical tip comprises a hub luer lock that is attachable to the anterior end of said cylinder and contains a luer tapered member and a luer locking member equipped with a screw member, such that said injection needle is fitted to said cylindrical tip via a needle base attached to said injection needle by means of fitting said needle base to said luer tapered member and engaging it with said screw member of said luer locking member; a mark indicating a position of the cutting surface on a circumference of said injection needle is provided on each exterior surface of said hub luer lock and said protector; and a position of said mark and a position of a scale display, provided on an exterior portion of said cylinder, are in alignment on a circumference of said cylinder.

3. A combined container-syringe according to claim 1, wherein said finger grip is constructed in a manner as to allow rotation around an axial circumference of said cylinder, such that the position, on the circumference of said cylinder, of a finger rest of said finger grip can be adjusted.

4. A combined container-syringe according to claim 2, wherein said finger grip is constructed in a manner as to allow rotation around an axial circumference of said cylinder, such that the position, on the circumference of said cylinder, of a finger rest of said finger grip can be adjusted.

5. A combined container-syringe according to claim 1, wherein said mark is also provided on an exterior surface of said finger grip.

6. A combined container-syringe according to claim 2, wherein said mark is also provided on an exterior surface of said finger grip.

7. A combined container-syringe according to claim 2, wherein said syringe body is formed by fitting a front assembly which including said cylindrical tip, said injection needle, and said protector, to the anterior end of said cylinder; and the position of the cutting surface of said injection needle is aligned by relatively rotating said front assembly around the axial circumference of said cylinder.

8. A combined container-syringe comprising a syringe body containing a cylindrical-shaped cylinder; a cylindrical tip provided at an anterior end of the cylinder; a finger grip provided at a posterior end of said cylinder and having a portion which indicates a predetermined position of the finger grip around an axial circumference of said cylinder; an injection needle fitted to said cylindrical tip; and a protector covering said injection needle; wherein, positions of a cutting surface of said injection needle and a scale display provided on an exterior portion of said cylinder are in alignment with said predetermined position of said finger grip, on a circumference of said cylinder.

9. A combined container-syringe according to claim 8, wherein, said finger grip is constructed in a manner as to allow rotation of a position of a finger rest of said finger grip, on the circumference of said cylinder, around the axial circumference of said cylinder.

10. A combined container-syringe according to claim 9, wherein an opening is provided in a radial direction of said finger grip.

11. A combined container-syringe according to claim 8, wherein said syringe body is formed by fitting a front assembly which including said cylindrical tip, said injection needle, and said protector, to the anterior end of said cylinder; and the position of the cutting surface of said injection needle is aligned by relatively rotating said front assembly around the axial circumference of said cylinder.

\* \* \* \* \*